(12) United States Patent
Slusher et al.

(10) Patent No.: US 11,766,423 B2
(45) Date of Patent: Sep. 26, 2023

(54) 2,6-DIMETHOXY-4-(5-PHENYL-4-THIOPHENE-2-YL-1H-IMIDAZOL-2-YL)-PHENOL (DPTIP) A SMALL MOLECULE INHIBITOR OF NEUTRAL SPHINGOMYELINASE 2 (NSMASE-2) FOR THE TREATMENT OF NEURODEGENERATIVE AND ONCOLOGIC DISEASES

(71) Applicants: THE JOHNS HOPKINS UNIVERSITY, Baltimore, MD (US); THE UNITED STATES OF AMERICA, AS REPRESENTED BY THE SECRETARY, DEPARTMENT OF HEALTH AND HUMAN SERVICES, OFFICE OF TECHNOLOGY TRANSFER, NATIONAL INSTITUTES OF HEALTH, Bethesda, MD (US)

(72) Inventors: Barbara Slusher, Kingsville, MD (US); Camilo Rojas, Baltimore, MD (US); Ajit G. Thomas, Baltimore, MD (US); Norman Haughey, Baltimore, MD (US); Marc Ferrer, Potomac, MD (US); Xin Hu, Frederick, MD (US)

( * ) Notice: Subject to any disclaimer, the term of this patent is extended or adjusted under 35 U.S.C. 154(b) by 258 days.

(21) Appl. No.: 16/977,305

(22) PCT Filed: Mar. 1, 2019

(86) PCT No.: PCT/US2019/020254
§ 371 (c)(1),
(2) Date: Sep. 1, 2020

(87) PCT Pub. No.: WO2019/169247
PCT Pub. Date: Sep. 6, 2019

(65) Prior Publication Data
US 2021/0000798 A1 Jan. 7, 2021

Related U.S. Application Data

(60) Provisional application No. 62/636,998, filed on Mar. 1, 2018.

(51) Int. Cl.
*A61K 31/4178* (2006.01)
*A61P 25/28* (2006.01)

(52) U.S. Cl.
CPC .......... *A61K 31/4178* (2013.01); *A61P 25/28* (2018.01)

(58) Field of Classification Search
CPC .......... A61K 21/4178; A61P 25/28; A61P 9/00
See application file for complete search history.

(56) References Cited

U.S. PATENT DOCUMENTS

2005/0203155 A1 9/2005 Salassidis et al.
2015/0044193 A1 2/2015 Manning-Bog et al.

FOREIGN PATENT DOCUMENTS

WO WO 92/04330 3/1992
WO WO 2004/016086 2/2004
WO WO 2016/141381 9/2016

OTHER PUBLICATIONS

Christopher J. Clarke, Yusuf A. Hannun, Neutral sphingomyelinases and nSMase2: Bridging the gaps, Biochimica et Biophysica Acta (BBA)—Biomembranes, vol. 1758, Issue 12, 2006, pp. 1893-1901, ISSN 0005-2736, https://doi.org/10.1016/j.bbamem.2006.06.025. (Year: 2006).*
Shamseddine AA, Airola MV, Hannun YA. Roles and regulation of neutral sphingomyelinase-2 in cellular and pathological processes. Adv Biol Regul. Jan. 2015;57:24-41. doi: 10.1016/j.jbior.2014.10. 002. Epub Oct. 27, 2014. PMID: 25465297; PMCID: PMC4684640. (Year: 2014).*
Bang C, et al.Cardiac fibroblast-derived microRNA passenger strand-enriched exosomes mediate cardiomyocyte hypertrophy. J Clin Invest. May 2014;124(5):2136-46. doi: 10.1172/JCI70577. Epub Apr. 17, 2014. PMID: 24743145; PMCID: PMC4001534. (Year: 2014).*
Kobina, E, et al. Blockade of exosome generation with GW4869 dampens the sepsis-induced inflammation and cardiac dysfunction, Biochimica et Biophysica Acta (BBA)—Molecular Basis of Disease, vol. 1852, Issue 11, 2015, pp. 2362-2371, ISSN 0925-4439, https://doi.org/10.1016/j.bbadis.2015.08.010. (Year: 2015).*
Figuera-Losada, M., et al. Cambinol, a novel inhibitor of neutral sphingomyelinase 2 shows neuroprotective properties. PLoS One. May 26, 2015;10(5):e0124481. doi: 10.1371/journal.pone.0124481. PMID: 26010541; PMCID: PMC4444023. (Year: 2015).*
Lang JK, et al. Inhibiting Extracellular Vesicle Release from Human Cardiosphere Derived Cells with Lentiviral Knockdown of nSMase2 Differentially Effects Proliferation and Apoptosis in Cardiomyocytes, Fibroblasts and Endothelial Cells In Vitro. PLoS One. Nov. 2, 2016;11(11) (Year: 2016).*
Jinyun Zhu, et al. Myocardial reparative functions of exosomes from mesenchymal stem cells are enhanced by hypoxia treatment of the cells via transferring microRNA-210 in an nSMase2-dependent way, Artificial Cells, Nanomedicine, and Biotechnology, 46:8, 1659-1670, DOI: 10.1080/21691401.2017.1388249 (Year: 2017).*
International Search Report and Written Opinin for PCT/US2019/020254, dated Jun. 14, 2019. 7 pages.

(Continued)

*Primary Examiner* — Amy L Clark
*Assistant Examiner* — Liyuan Mou
(74) *Attorney, Agent, or Firm* — CASIMIR JONES, S.C.; Jeffery W. Childers

(57) ABSTRACT

Methods for treating one or more diseases associated with neutral sphingomyelinase 2 (nSMase2) in a subject in need of treatment thereof, the method comprising administering to the subject a therapeutically effective amount of 2,6-dimethoxy-4-(5-phenyl-4-thiophen-2-yl-1H-imidazol-2-yl)-phenol (DPTIP) or a pharmaceutically acceptable salt thereof, are disclosed.

2 Claims, 17 Drawing Sheets

(56) References Cited

OTHER PUBLICATIONS

Airola et al., Structure of human nSMase2 reveals an interdomain allosteric activation mechanism for ceramide generation. Proc Natl Acad Sci U S A. Jul. 11, 2017;114(28):E5549-E5558.
Alessenko et al., Connection of lipid peroxide oxidation with the sphingomyelin pathway in the development of Alzheimer's disease. Biochem Soc Trans. Feb. 2004;32(Pt 1):144-6.
Amor et al., Inflammation in neurodegenerative diseases—an update. Immunology. Jun. 2014;142(2):151-66.
Asai et al., Depletion of microglia and inhibition of exosome synthesis halt tau propagation. Nat Neurosci. Nov. 2015;18(11):1584-93.
Back et al., Activation of neutral sphingomyelinase 2 by starvation induces cell-protective autophagy via an increase in Golgi-localized ceramide. Cell Death Dis. Jun. 4, 2018;9(6):670. 18 pages.
Berge et al, "Pharmaceutical Salts", J Pharm Sci. Jan. 1977;66(1):1-19.
Chen et al., Endolysosome involvement in HIV-1 transactivator protein-induced neuronal amyloid beta production. Neurobiol Aging. Oct. 2013;34(10):2370-8.
Cutler et al., Evidence that accumulation of ceramides and cholesterol esters mediates oxidative stress-induced death of motor neurons in amyotrophic lateral sclerosis. Ann Neurol. Oct. 2002;52(4):448-57.
Dickens et al., Astrocyte-shed extracellular vesicles regulate the peripheral leukocyte response to inflammatory brain lesions. Sci Signal. Apr. 4, 2017;10(473):eaai7696. 13 pages.
Dinkins et al., Exosome reduction in vivo is associated with lower amyloid plaque load in the 5XFAD mouse model of Alzheimer's disease. Neurobiol Aging. Aug. 2014;35(8):1792-800.
Dinkins et al., Neutral Sphingomyelinase-2 Deficiency Ameliorates Alzheimer's Disease Pathology and Improves Cognition in the 5XFAD Mouse. J Neurosci. Aug. 17, 2016;36(33):8653-67.
Figuera-Losada et al., Cambinol, a novel inhibitor of neutral sphingomyelinase 2 shows neuroprotective properties. PLoS One. May 26, 2015;10(5):e0124481. 18 pages.
Filippov et al., Increased ceramide in brains with Alzheimer's and other neurodegenerative diseases. J Alzheimers Dis. 2012;29(3):537-47.
Goetzl et al., High complement levels in astrocyte-derived exosomes of Alzheimer disease. Ann Neurol. Mar. 2018;83(3):544-552.
Gu et al., Early activation of nSMase2/ceramide pathway in astrocytes is involved in ischemia-associated neuronal damage via inflammation in rat hippocampi. J Neuroinflammation. Sep. 3, 2013;10:109. 16 pages.
Haughey et al., Perturbation of sphingolipid metabolism and ceramide production in HIV-dementia. Ann Neurol. Feb. 2004;55(2):257-67.
Horres et al., The roles of neutral sphingomyelinases in neurological pathologies. Neurochem Res. Jun. 2012;37(6):1137-49.
Hu et al., Exosome-mediated shuttling of microRNA-29 regulates HIV Tat and morphine-mediated neuronal dysfunction. Cell Death Dis. Aug. 30, 2012;3(8):e381. 10 pages.
Ibrahim et al., Exosomes: Fundamental Biology and Roles in Cardiovascular Physiology. Annu Rev Physiol. 2016;78:67-83.
Inglese et al., Quantitative high-throughput screening: a titration-based approach that efficiently identifies biological activities in large chemical libraries. Proc Natl Acad Sci U S A. Aug. 1, 2006;103(31):11473-8.
Jana et al., Ceramide and neurodegeneration: susceptibility of neurons and oligodendrocytes to cell damage and death. J Neurol Sci. Mar. 15, 2009;278(1-2):5-15.
Jana et al., Fibrillar amyloid-beta-activated human astroglia kill primary human neurons via neutral sphingomyelinase: implications for Alzheimer's disease. J Neurosci. Sep. 22, 2010;30(38):12676-89.
Jana et al., Human immunodeficiency virus type 1 gp120 induces apoptosis in human primary neurons through redox-regulated activation of neutral sphingomyelinase. J Neurosci. Oct. 27, 2004;24(43):9531-40.

Jana et al., Sphingolipids in multiple sclerosis. Neuromolecular Med. Dec. 2010;12(4):351-61.
Kosaka et al., Neutral sphingomyelinase 2 (nSMase2)-dependent exosomal transfer of angiogenic microRNAs regulate cancer cell metastasis. J Biol Chem. Apr. 12, 2013;288(15):10849-59.
Kull et al., Mixturs of quaternary ammonium compounds and long-chain fatty acids as antifungal agents. Appl Microbiol. Nov. 1961;9(6):538-41.
Lee et al., Exosomes and microvesicles: extracellular vesicles for genetic information transfer and gene therapy. Hum Mol Genet. Oct. 15, 2012;21(R1):R125-34.
Li et al., α-TEA-induced death receptor dependent apoptosis involves activation of acid sphingomyelinase and elevated ceramide-enriched cell surface membranes. Cancer Cell Int. Oct. 25, 2010;10:40. 14 pages.
Livak et al., Analysis of relative gene expression data using real-time quantitative PCR and the 2(-Delta Delta C(T)) Method. Methods. Dec. 2001;25(4):402-8.
Lotvall et al., Minimal experimental requirements for definition of extracellular vesicles and their functions: a position statement from the International Society for Extracellular Vesicles. J Extracell Vesicles. Dec. 22, 2014;3:26913. 6 pages.
Luberto et al., Inhibition of tumor necrosis factor-induced cell death in MCF7 by a novel inhibitor of neutral sphingomyelinase. J Biol Chem. Oct. 25, 2002;277(43):41128-39.
Marks et al., Glucosylceramide synthase decrease in frontal cortex of Alzheimer brain correlates with abnormal increase in endogenous ceramides: consequences to morphology and viability on enzyme suppression in cultured primary neurons. Brain Res. Jan. 29, 2008;1191:136-47.
Mathias et al., Activation of the sphingomyelin signaling pathway in intact EL4 cells and in a cell-free system by IL-1 beta. Science. Jan. 22, 1993;259(5094):519-22.
Mccluskey et al., Inflammatory responses in the rat brain in response to different methods of intra-cerebral administration. J Neuroimmunol. Feb. 2008;194(1-2):27-33.
Menck et al., Neutral sphingomyelinases control extracellular vesicles budding from the plasma membrane. J Extracell Vesicles. Sep. 26, 2017;6(1):1378056. 15 pages.
Mielke et al., Disturbance in cerebral spinal fluid sphingolipid content is associated with memory impairment in subjects infected with the human immunodeficiency virus. J Neurovirol. Nov. 2010;16(6):445-56.
Mielke et al., Plasma ceramides are altered in mild cognitive impairment and predict cognitive decline and hippocampal volume loss. Alzheimers Dement. Sep. 2010;6(5):378-85.
Rais et al., Discovery of 6-Diazo-5-oxo-l-norleucine (DON) Prodrugs with Enhanced CSF Delivery in Monkeys: A Potential Treatment for Glioblastoma. J Med Chem. Sep. 22, 2016;59(18):8621-33.
Raposo et al., Extracellular vesicles: exosomes, microvesicles, and friends. J Cell Biol. Feb. 18, 2013;200(4):373-83.
Satoi et al., Astroglial expression of ceramide in Alzheimer's disease brains: a role during neuronal apoptosis. Neuroscience. 2005;130(3):657-66.
Shamseddine et al., Roles and regulation of neutral sphingomyelinase-2 in cellular and pathological processes. Adv Biol Regul. Jan. 2015;57:24-41.
Shin et al., Serum-starvation induces the extracellular appearance of FGF-1. Biochim Biophys Acta. Jun. 5, 1996;1312(1):27-38.
Sjoblom et al., Alpha-actinin structure and regulation. Cell Mol Life Sci. Sep. 2008;65(17):2688-701.
Trajkovic et al., Ceramide triggers budding of exosome vesicles into multivesicular endosomes. Science. Feb. 29, 2008;319(5867):1244-7.
Van Echten-Deckert et al., Sphingolipids: critical players in Alzheimer's disease. Prog Lipid Res. Oct. 2012;51(4):378-93.
Von Der Malsburg et al., Dual role of mitofilin in mitochondrial membrane organization and protein biogenesis. Dev Cell. Oct. 18, 2011;21(4):694-707.
Wang et al., Long-chain ceramide is elevated in presenilin 1 (PS1M146V) mouse brain and induces apoptosis in PS1 astrocytes. Glia. Mar. 2008;56(4):449-56.

(56) References Cited

OTHER PUBLICATIONS

Weidle et al., The Multiple Roles of Exosomes in Metastasis. Cancer Genomics Proteomics. Jan. 2, 2017;14(1):1-15.

Westberry et al., Epigenetic regulation of estrogen receptor alpha gene expression in the mouse cortex during early postnatal development. Endocrinology. Feb. 2010;151(2):731-40.

Wheeler et al., TNFα-induced neutral sphingomyelinase-2 modulates synaptic plasticity by controlling the membrane insertion of NMDAreceptors. J Neurochem. Jun. 2009;109(5):1237-49.

Wu et al., Mammalian neutral sphingomyelinases: regulation and roles in cell signaling responses. Neuromolecular Med. Dec. 2010;12(4):320-30.

* cited by examiner

DPTIP – $IC_{50} = 50 \pm 0.3$ nM
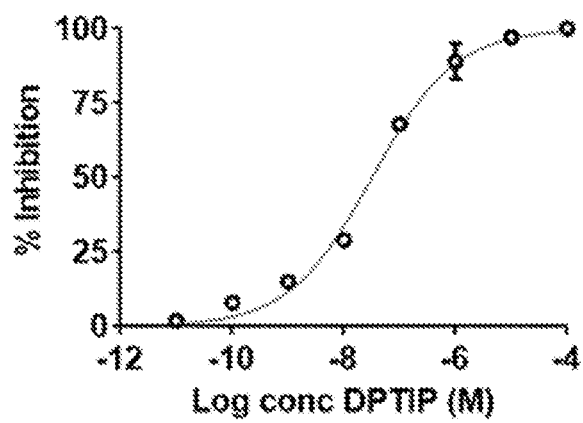
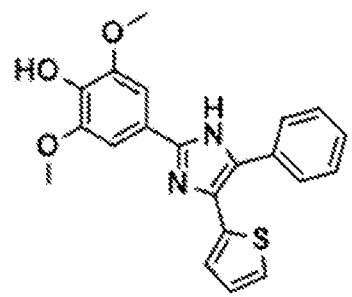
*Fig. 3A*

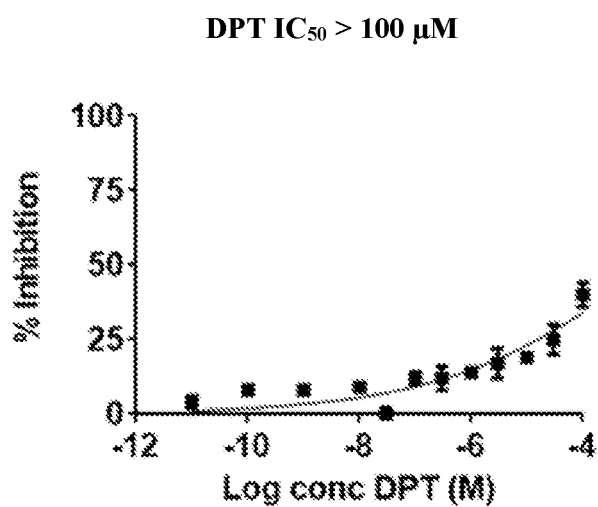
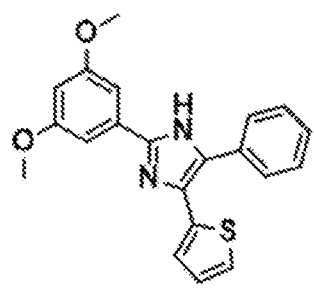
Fig. 3B

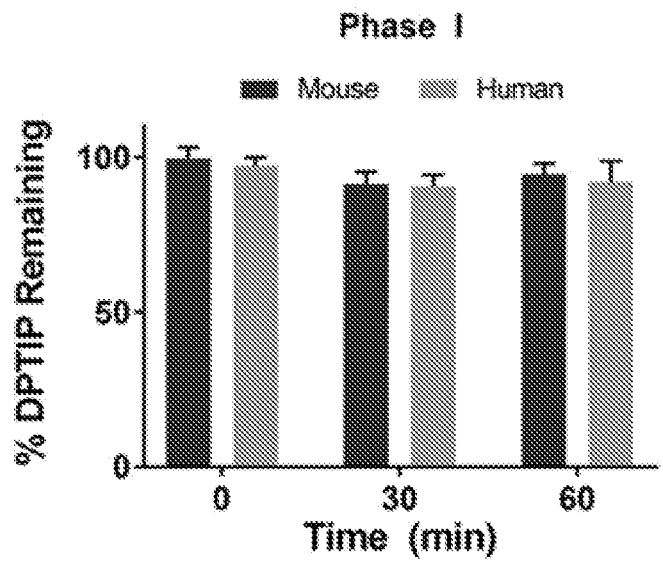
*Fig. 4A*
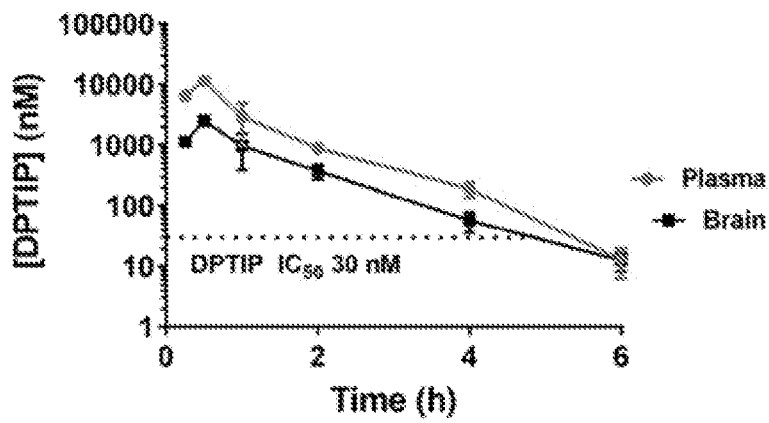
*Fig. 4B*
| | Tmax (h) | Cmax (µM) | AUC (µM * h) |
|---|---|---|---|
| Plasma | 0.5 | 11.6 ± 0.5 | 10 ± 1 |
| Brain | 0.5 | 2.5 ± 0.2 | 2.6 ± 0.5 |
*Fig. 4C*

| Protocol: | | | |
|---|---|---|---|
| Step | Parameter | Value | Description |
| 1 | Enzyme: human nSMase2 in whole cell lysate | 2 μl/well | 0.2 μg/μl as 2x working concentration in 1x reaction buffer on black NB solid bottom 1536-well plate (Greiner 789176-F); columns(c.) 1, 3, 5-48 |
| 2 | "No enzyme" as (-) control (IC100) | 2 μl/well | 1x reaction buffer ~ column 2 |
| 3 | (+) control | 2 μl/well | Bacterial enzyme at 0.04 U/ml as 2x working concentration ~ c.4 |
| 4 | Centrifugation | 1000 rpm, 20 sec | |
| 5 | Controls/Compounds | 23 nL | Control plate: Cambinol 50 mM, dose response 1:2 dilutions ~ c.1, GW4869 50 mM dose response 1:2 dilutions ~ c.3, DMSO ~ c.2,4. |
| 6 | Pre-incubation Time | 15 min | Ambient temperature |
| 7 | Reaction mix with Substrate (SM): | 2 μl/well | Amplex Red + HRP + Choline oxidase + Alkaline phosphatase mix containing 0.04 mM Sphingomyelin as 2X working concentration to all wells |
| 8 | Centrifugation | 1000 rpm, 20 sec | |
| 9 | Incubation Time | 120 min | 37°C |
| 10 | Detection | Viewlux | Fluorescent settings: Excitation 525 / Emission 598, Energy 1000, Exposure 8 sec |

| Step | Notes |
|---|---|
| 1 | Keep enzyme on ice all the time |
| 4 | Due to small volume, must make sure the compounds will get into enzyme's volume |
| 7 | Keep the substrate mix on ice, PROTECT FROM LIGHT the bottle and the tubing. Keep the light dimmed in the room |
| 9 | Pre-read to exclude fluorescent compounds |

*Fig. 8*

2,6-DIMETHOXY-4-(5-PHENYL-4-THIOPHENE-2-YL-1H-IMIDAZOL-2-YL)-PHENOL (DPTIP) A SMALL MOLECULE INHIBITOR OF NEUTRAL SPHINGOMYELINASE 2 (NSMASE-2) FOR THE TREATMENT OF NEURODEGENERATIVE AND ONCOLOGIC DISEASES

FEDERALLY SPONSORED RESEARCH OR DEVELOPMENT

This invention was made with government support under grant number MH107659 awarded by the National Institutes of Health. The government has certain rights in this invention.

BACKGROUND

Brains from Alzheimer's disease (AD) patients show elevated ceramide, an integral component of exosomal membranes. One major source of ceramide is through the hydrolysis of sphingomyelin catalyzed by neutral sphingomyelinase 2 (nSMase2). Recent studies show that chronically activated nSMase2 is implicated in both Aβ aggregation and tau propagation through its role in exosome secretion. Moreover, genetic and pharmacological inhibition of nSMase2 has been shown to reduce Aβ aggregation and tau propagation and to attenuate cognitive deficits in multiple preclinical AD models, opening a new avenue for the development of AD therapeutics. Unfortunately, currently available nSMase2 inhibitors have low potency, poor solubility, and limited brain penetration.

SUMMARY

The presently disclosed subject matter provides methods for treating one or more diseases associated with neutral sphingomyelinase 2 (nSMase2) in a subject in need of treatment thereof, the method comprising administering to the subject a therapeutically effective amount of 2,6-dimethoxy-4-(5-phenyl-4-thiophen-2-yl-1H-imidazol-2-yl)-phenol (DPTIP) or a pharmaceutically acceptable salt thereof.

In some aspects, the one or more diseases associated with neutral sphingomyelinase 2 (nSMase2) results in an elevated level of ceramide in the subject.

In particular aspects, the one or more diseases associated with neutral sphingomyelinase 2 (nSMase2) is selected from the group consisting of a neurodegenerative disease, an oncologic disease, and a cardiac disease.

In yet more particular aspects, the neurodegenerative disease is selected from the group consisting of Alzheimer's disease (AD), multiple sclerosis (MS), amyotrophic lateral sclerosis (ALS), and HIV-associated neurocognitive disorders (HAND).

In certain aspects, the cardiac disease is a myocardial disease involving myocyte hypertrophy, fibroblast-derived cardiac hypertrophy, heart failure, heart hypertrophy, diastolic and/or systolic ventricular dysfunction and/or a cardiovascular disease involving fibrosis, aortic stenosis, atrial fibrillation, genetic forms of cardiomyopathy, cardiac storage diseases and/or fabry disease.

In other aspects, the presently disclosed subject matter provides a method for inhibiting neutral sphingomyelinase 2 (nSMase2), the method comprising contacting a cell comprising nSMase2 with an amount of 2,6-dimethoxy-4-(5-phenyl-4-thiophen-2-yl-1H-imidazol-2-yl)-phenol (DPTIP) or a pharmaceutically acceptable salt thereof.

In other aspects, the presently disclosed subject matter provides a method for inhibiting exosome biosynthesis, the method comprising contacting a cell with an amount of 2,6-dimethoxy-4-(5-phenyl-4-thiophen-2-yl-7H-imidazol-2-yl)-phenol (DPTIP) or a pharmaceutically acceptable salt thereof.

In yet other aspects, the presently disclosed subject matter provides a method for inhibiting ceramide biosynthesis, the method comprising contacting a cell with an amount of 2,6-dimethoxy-4-(5-phenyl-4-thiophen-2-yl-1H-imidazol-2-yl)-phenol (DPTIP) or a pharmaceutically acceptable salt thereof.

In even yet other aspects, the presently disclosed subject matter provides for the use of 2,6-dimethoxy-4-(5-phenyl-4-thiophen-2-yl-1H-imidazol-2-yl)-phenol (DPTIP) for the production of a medicament for treating one or more diseases associated with neutral sphingomyelinase 2 (nSMase2).

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

The patent or application file contains at least one drawing executed in color. Copies of this patent or patent application publication with color drawings will be provided by the Office upon request and payment of the necessary fee.

Figure 1A:
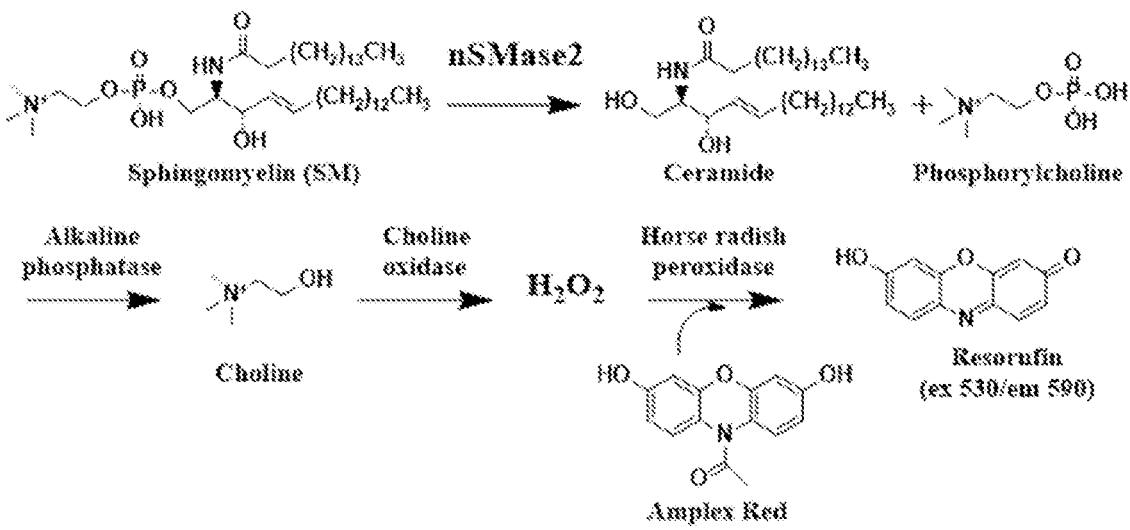
Figure 1B:
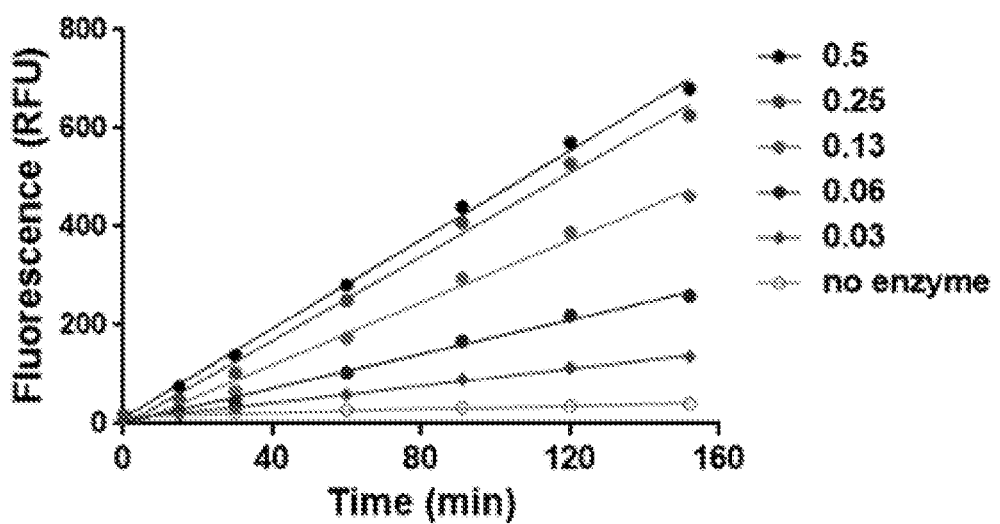
Figure 1C:
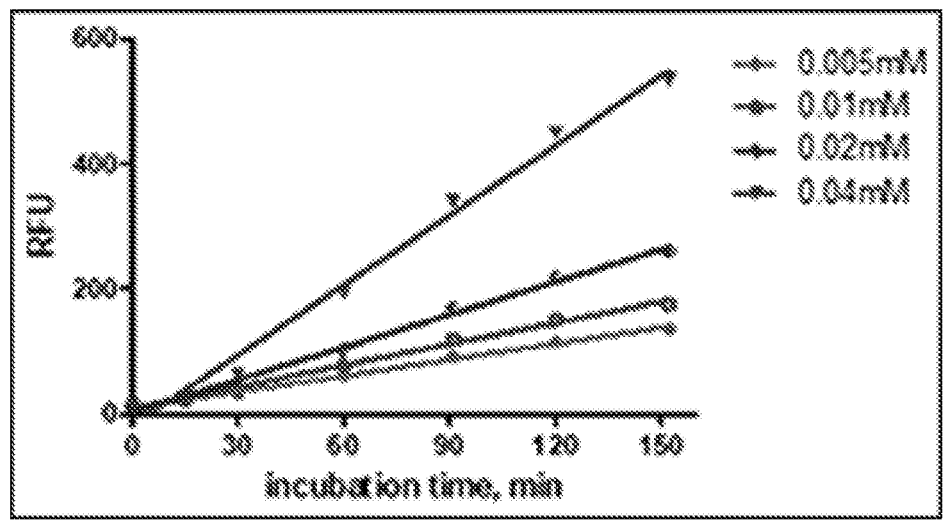
Figure 1D:
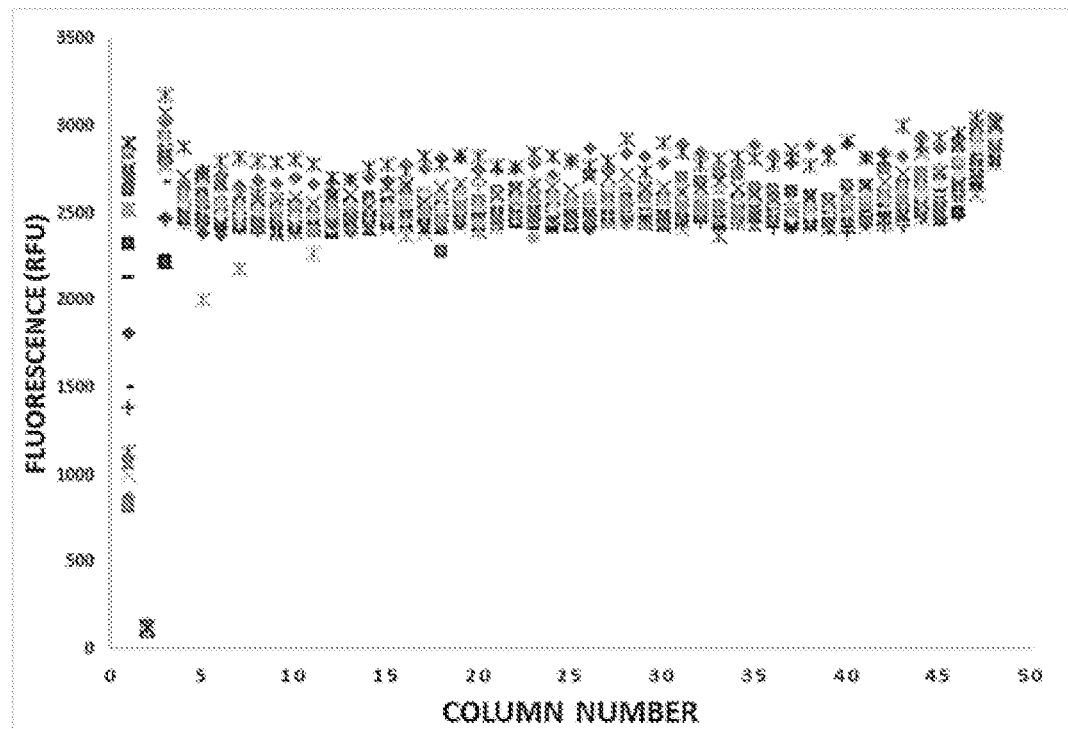
Figure 1E:
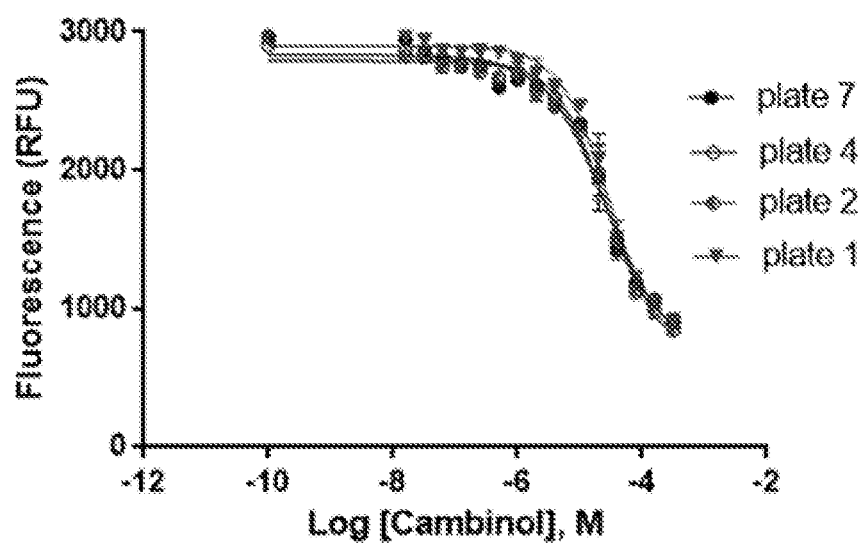
Figure 2A:
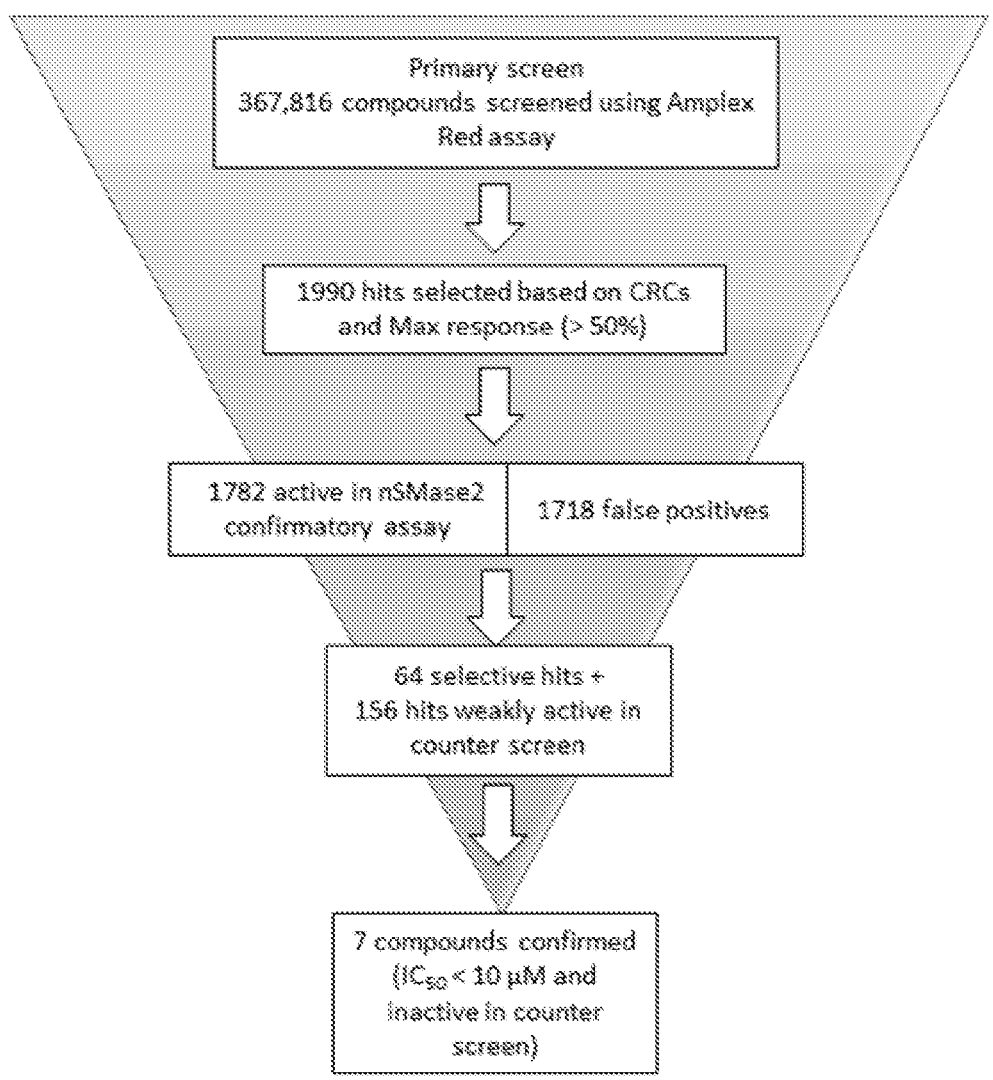
Figure 2B:
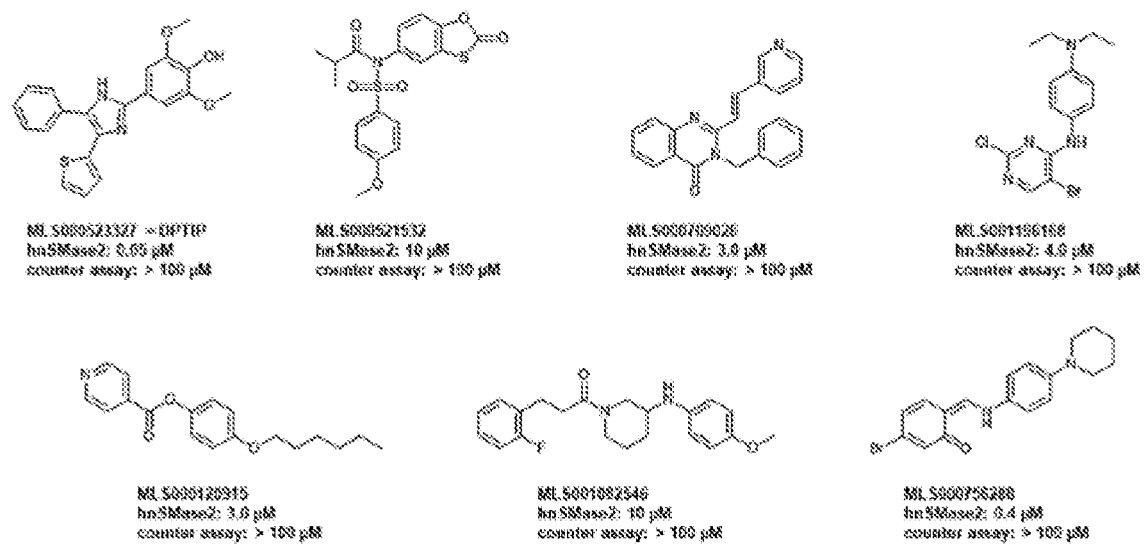
Figure 3C:
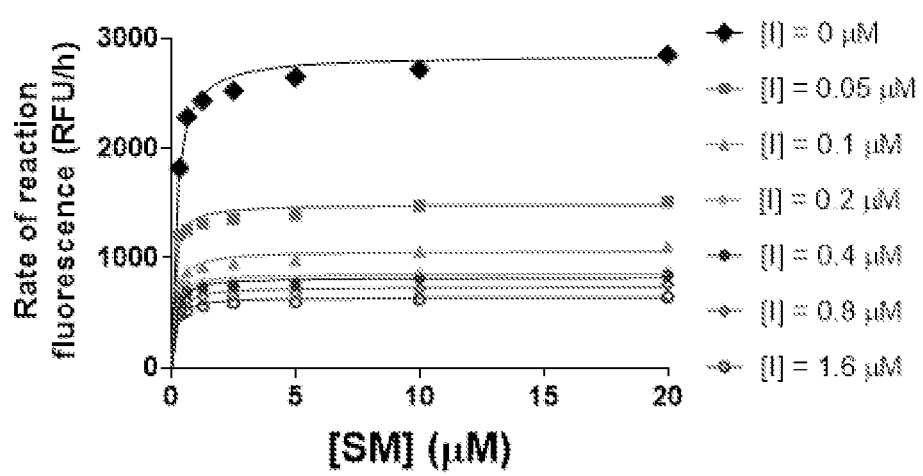
Figure 5A:
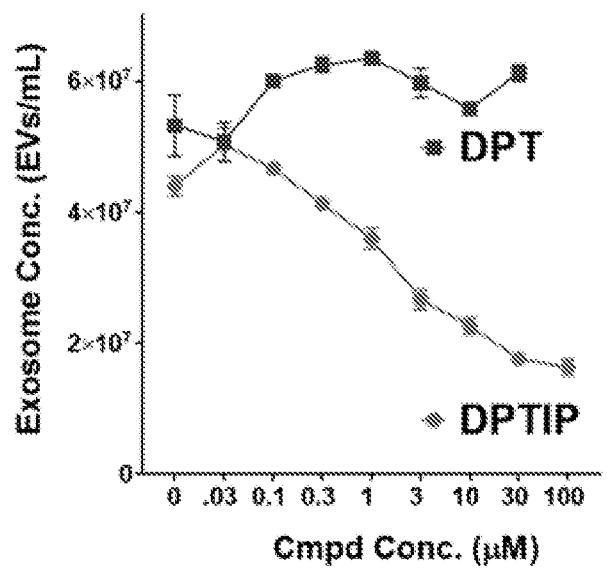
Figure 5B:
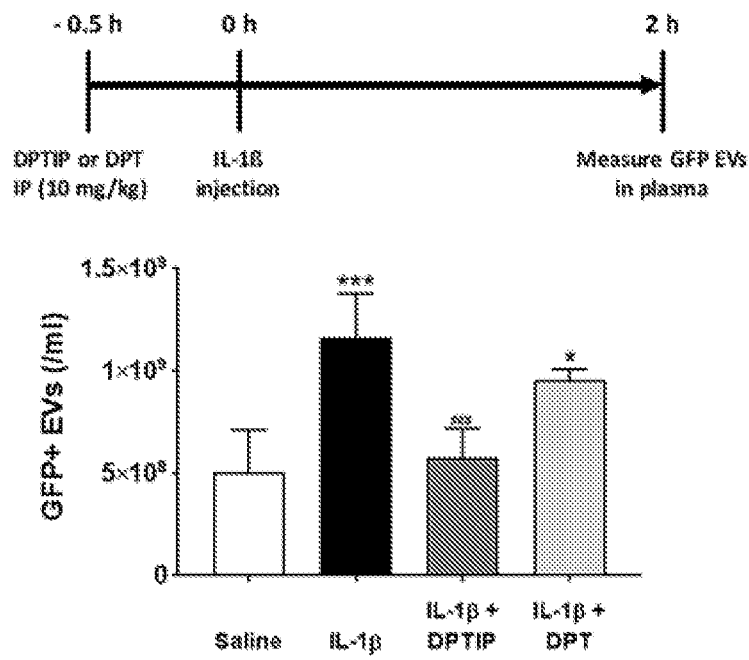
Figure 5C:
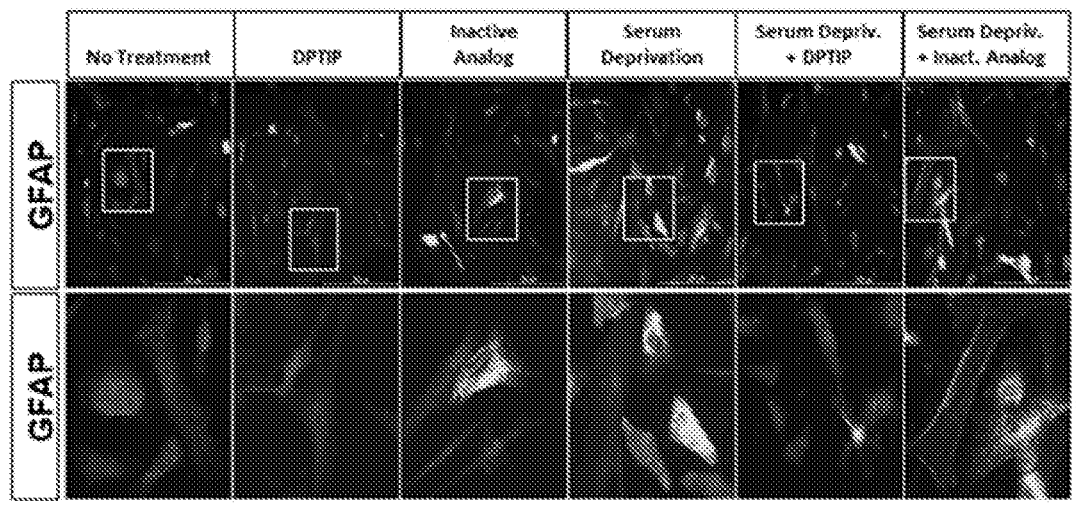
Figure 6A:
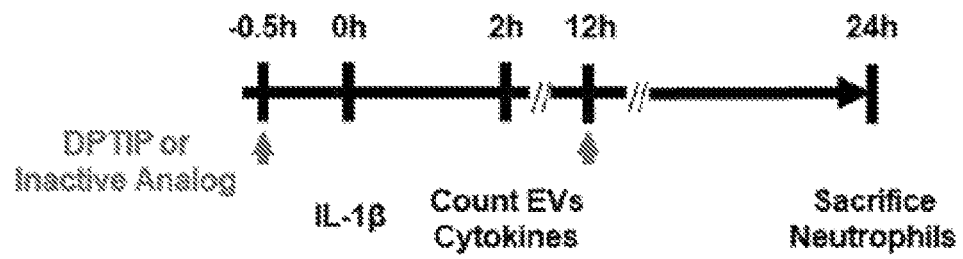
Figure 6B:
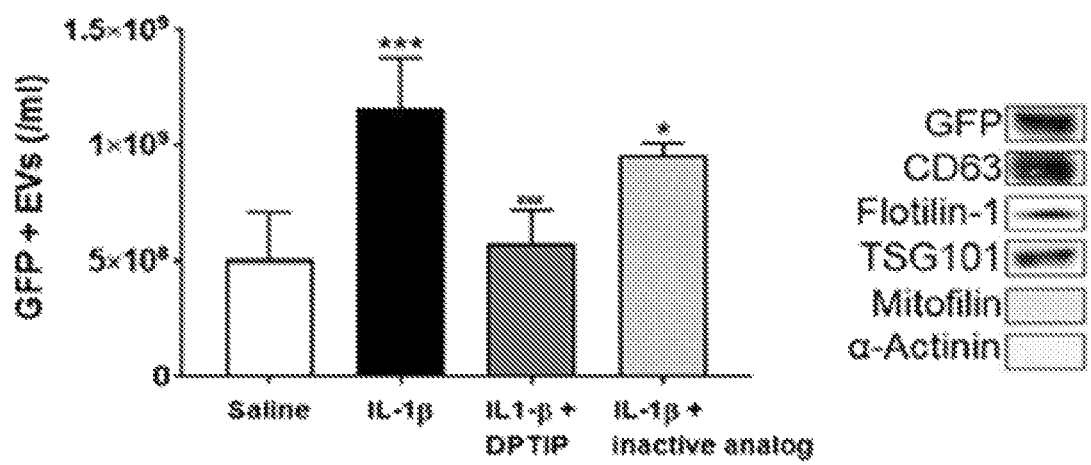
Figure 6C:
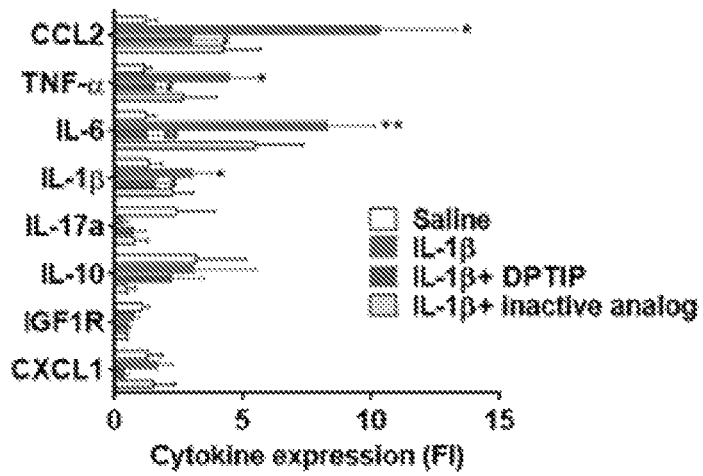
Figure 6D:
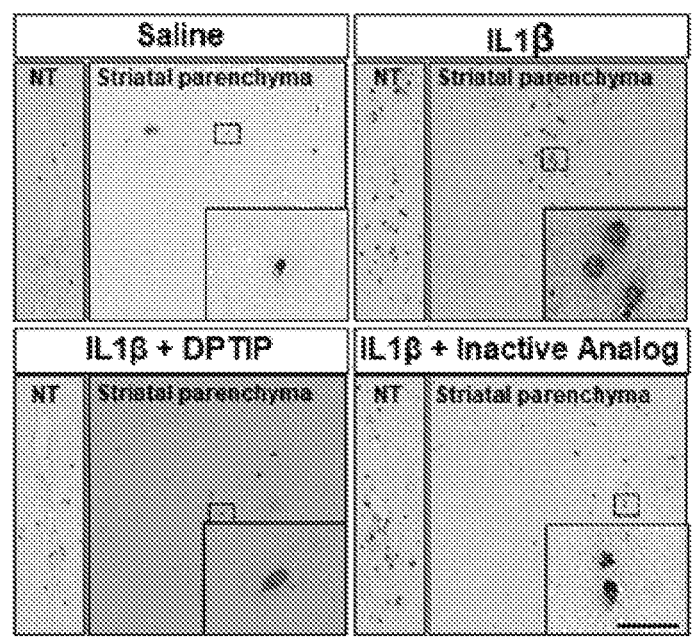
Figure 6E:
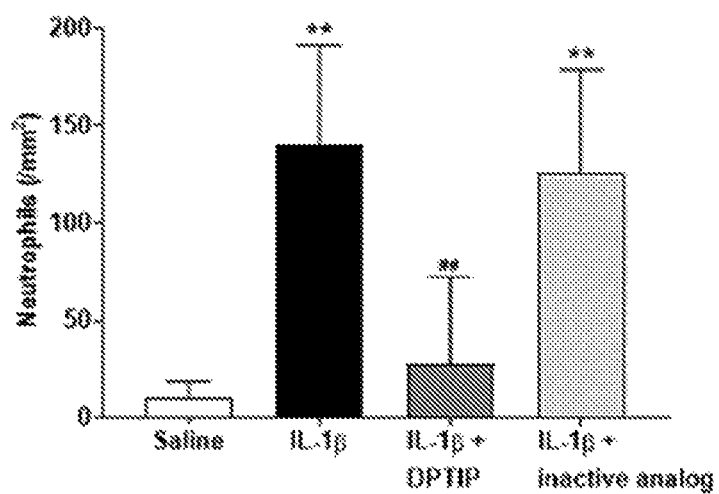
Figure 7:
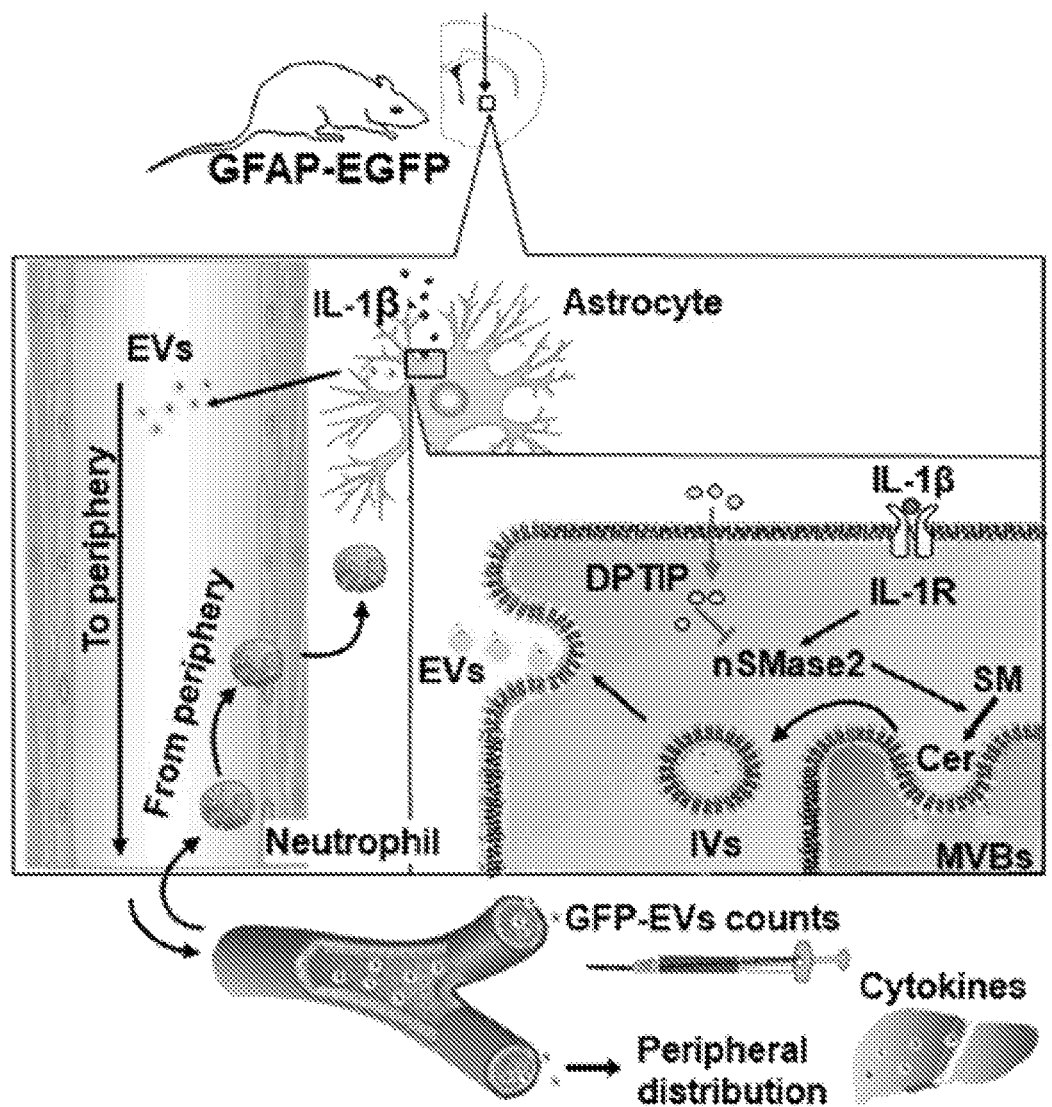

Having thus described the presently disclosed subject matter in general terms, reference will now be made to the accompanying Figures, which are not necessarily drawn to scale, and wherein:

FIG. 1A, FIG. 1B, FIG. 1C, FIG. 1D, and FIG. 1E show validation of the human nSMase2 fluorescence-based assay in 1536-well format to screen for inhibitors of the enzyme in dose response quantitative high throughput screening (qHTS). FIG. 1A is a schematic representation of the assay. Human nSMase2 catalyzes the hydrolysis of sphingomyelin (SM) to ceramide and phosphorylcholine. Using alkaline phosphatase, choline oxidase, horse radish peroxidase and Amplex Red, phosphorylcholine is stoichiometrically converted through enzyme-coupled reactions to fluorescent resorufin; fluorescence is directly proportional to nSMase2 activity. FIG. 1B shows the dependence of fluorescence signal on time of incubation (in min) at several enzyme concentrations (0.03 to 0.5 μg protein/μL) in the presence of 20 μM SM. FIG. 1C shows the dependence of fluorescence signal on time of incubation at different SM concentrations (0.005 to 0.04 mM) in the presence of 0.063 μg protein/μL. FIG. 1D is a scatter plot of fluorescence signal from a 1536-well assay plate. Human nSMase2 cell lysate (0.1 μg/μL) was incubated with SM (20 μM) and coupling reagents for 2 h at 37° C. before measuring fluorescence. When using cambinol as positive control, compound was preincubated with human nSMase2 for 15 min. Column 1: Cambinol dose response. Column 2: Negative control (no enzyme). Column 3: Positive control (bacterial SMase 0.02 U/mL). Columns 4-48 human nSMase2 (Final DMSO concentration: 0.57%). Fluorescence signal is expressed as relative fluorescent units (RFU) on the y-axis. Plate number is shown on x-axis. FIG. 1E shows the dose response of inhibition of nSMase2 by cambinol, a known inhibitor of nSMase2 (Figura-Losada, et al., 2015). Wells contained cell lysate prepared from cells expressing nSMase2 (0.1 μg/μL)

and SM (20 µM) with increasing concentrations of cambinol as indicated. During the screen, cambinol was used to track plate-to-plate variability; it was delivered onto each plate in 16 doses, at 1:2 dilutions in the range 285 µM-17 nM;

FIG. 2A and FIG. 2B demonstrate the identification of nSMase2 inhibitors from qHTS. FIG. 2A is a flowchart illustrating the filtering of HTS hits that led to the confirmation of 7 nSMase2 inhibitors with $IC_{50}$<50 µM that were inactive in the counter assay. CRC: curve response classes. FIG. 2B shows structures of the 7 human nSMase2 inhibitors with corresponding $IC_{50}$s for inhibition of human nSMase2. Alkaline phosphatase >100 µM means compounds did not show inhibition of fluorescence at 100 µM in the counter assay where all coupling reagents were present and SM was replaced by phosphorylcholine (2 µM), the substrate for alkaline phosphatase;

FIG. 3A, FIG. 3B, and FIG. 3C show inhibition of nSMase2 by (FIG. 3A) DPTIP and (FIG. 3B) its inactive des-hydroxyl analog, 2-(3,5-dimethoxyphenyl)-5-phenyl-4-(thiophen-2-yl)-1H-imidazole (DPT). Human nSMase2 (0.1 µg/µL) was added to a reaction mixture containing SM (20 µM), coupling reagents and DPTIP or DPT in the 10 pM-100 µM range. Percent inhibition was obtained from [(rate of change of fluorescence in the presence of inhibitor divided by rate of change of fluorescence in the absence of inhibitor)×100]. Each data point corresponds to the average of two independent experiments run in replicate. Error bars correspond to S.E.M. FIG. 3C shows the rate of reaction vs concentration of SM in the presence of several DPTIP concentrations. Human nSMase2 cell lysate (0.1 µg/µL) was incubated with increasing concentrations of SM and coupling reagents for 2 h at 37° C. before measuring fluorescence. $V_{max}$ and $K_m$ values were obtained from non-linear regression fits to Michaelis-Menten kinetics using prism;

FIG. 4A, FIG. 4B, and FIG. 4C demonstrate the metabolic stability and in vivo pharmacokinetics of DPTIP. FIG. 4A shows the metabolic stability in mouse and human liver microsomes. DPTIP was stable in mouse and human liver microsomes fortified with NADPH suggesting stability to phase I oxidation; percent DPTIP remaining was determined by liquid chromatography-tandem mass spectrometry analysis (LC/MS/MS). FIG. 4B shows the plasma and brain profiles following 10 mg/kg i.p. dose; n=3 at each time point. FIG. 4C shows the pharmacokinetic parameters calculated from traces in (FIG. 4B);

FIG. 5A, FIG. 5B, FIG. 5C, and FIG. 5D demonstrate inhibition of exosome release by DPTIP in astrocytes in vitro. (FIG. 5A) Rat primary astrocytes were treated in parallel incubations with DPTIP or its des-hydroxy inactive analog (DPT) at 0.3, 1, 3, and 10 µM; DMSO (0.02%) was used as vehicle control. Media was collected after 2 h incubation and centrifuged at 2700 g for 15 minutes at 4° C. Supernatant was collected and the number of extracellular vesicles (EVs) was quantified using ZetaView Nanoparticle Tracker. The mean concentration of EVs/mL (±SEM) was calculated from 4 replicate experiments. FIG. 5B demonstrates inhibition of exosome release in vivo. Mice were given DPTIP or DPT (10 mg/kg IP) followed by striatal injections of saline or IL-1β as indicated. GFP-containing exosomes released from astrocytes in the brain were quantified in plasma of mice 2.5 h following compound administration. Data are mean±SD, n=5-10 mice per condition. *, p<0.05 compared to saline control; ###, p<0.001 compared to IL1-β group; ***, p<0.001 compared to saline group. There was no significant difference observed between IL-1β and IL-1β plus DPT groups. (FIG. 5C) Rat primary astrocytes were treated with DPTIP or inactive analog (+/−) serum-deprivation-induced stress for 2 h. Astrocytes grown in complete medium were used as no treatment control. Cells were fixed and stained with anti-GFAP antibody (1:500, Sigma). Fluorescence intensity was measured using Image J. (FIG. 5D) Quantitation of fluorescence in (FIG. 5C). Bar graph represents background corrected mean fluorescence intensity measured from 100 astrocytes per condition. Error bars represent standard error of mean. One-way ANOVA followed by Tukey's posthoc test was performed;

FIG. 6A, FIG. 6B, FIG. 6C, FIG. 6D, and FIG. 6E show the effects of DPTIP in mouse model of brain inflammation. FIG. 6A is the Experiment Timeline—Four groups of GFAP-EGFP mice were administered saline, IL-1β, IL1-β+DPTIP (10 mg/kg) or IL-1β+inactive analog (10 mg/kg). Compounds were given 0.5 h before IL-1β dosing. One group of mice was sacrificed 2 h after IL-1β administration to determine effects of the various treatments on extracellular vesicles (EVs) releases from brain and liver cytokine analysis. The second group was dosed a second time 12 h after IL-1β administration and sacrificed at 24 h to evaluate the effects of different treatments on neutrophil infiltration into brain. FIG. 6B shows GFP-labeled EVs in plasma under different treatments. Data are mean±SD, n=5 mice per condition. *p<0.05 compared to saline control; ###p<0.001 compared to IL1-β group; *p<0.001 compared to saline group. There was no difference observed between IL-1β and IL-1β plus des-hydroxyl analog groups. Panel to the right shows Western blot analysis using EVs when evaluating against GFP, exosomal (CD63, flotilin-1, TSG101), mitochondrial (mitofilin) and cytoskeletal (α-actinin) markers. FIG. 6C shows liver cytokine levels under different treatments as measured by qRT-PCR of RNA isolated from fresh frozen liver tissue. Samples were analyzed in triplicate. p<0.01 and *p<0.05 compared to saline control; ##p<0.01 and #p<0.05 compared to IL1-β group. FIG. 6D shows neutrophil levels in brain as measured by immunohistochemistry using coronal brain sections and Ly6b antibody; and FIG. 6E shows quantitation of FIG. 6D; **p<0.01 compared to saline control; ##p<0.01 compared to IL1-β group;

FIG. 7 is the proposed mechanism for the role of nSMase2 during inflammatory brain injury and effect of nSMase2 inhibition by DPTIP—Intracerebral injection of IL-1β activates the IL-1β receptor which in turn activates nSMase2. nSMase2-catalyzed hydrolysis of sphingomyelin (SM) produces long-chain ceramides (Cer). Increase in ceramide production at multivesicular bodies (MVBs) leads to the formation of intraluminal vesicles (IVs) and budding of extracellular vesicles (EVs) that are then shed from astrocytes and released into the periphery. Astrocyte-generated EVs can be identified in plasma because they are GFP-labeled. Astrocytic EVs promote crossing of neutrophils into brain as a result of cytokine upregulation in liver. In the presence of DPTIP, nSMase2 is inhibited, ceramide is not available for EV biosynthesis resulting in blockade of both cytokine upregulation and neutrophil infiltration;

FIG. 8 is a detailed HTS assay protocol; and

Figure 9:
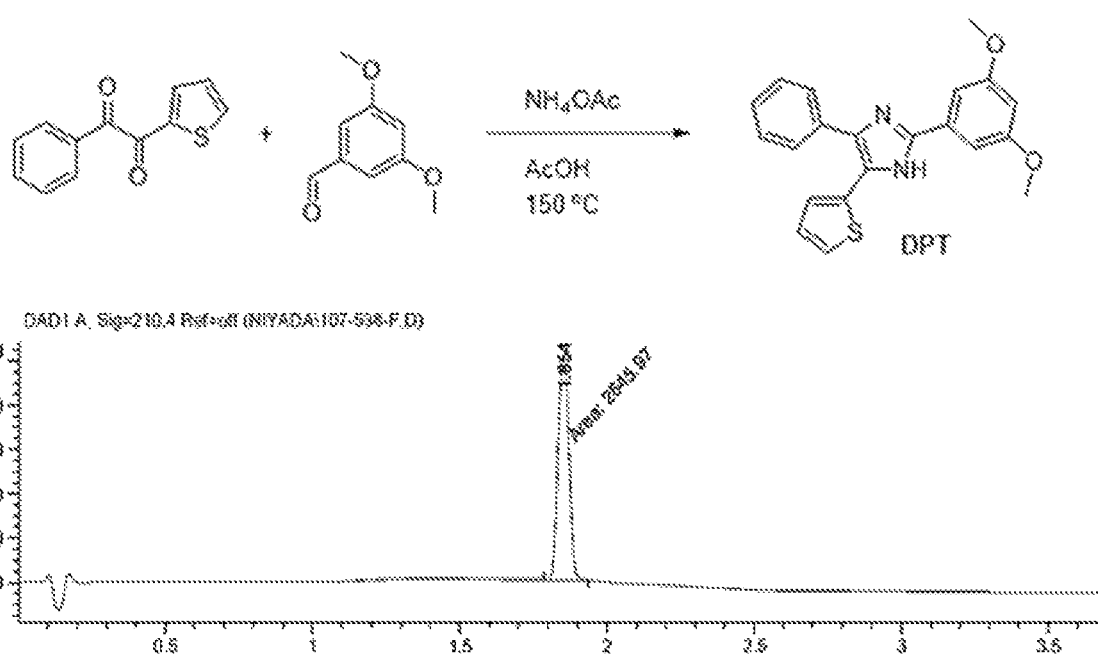

FIG. 9 shows the synthesis scheme and authentication of DPT.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Discovery of 2,6-dimethoxy-4-(5-phenyl-4-thiophene-2-yl-1H-imidazol-2-yl)-phenol (DPTIP) a Small Molecule Inhibitor of Neutral Sphingomyelinase 2 (nSMase-2) for the Treatment of Neurodegenerative and Oncologic Diseases In some embodiments, the presently disclosed subject matter discloses the discovery of 2,6-dimethoxy-4-(5-phenyl-4-thiophen-2-yl-1H-imidazol-2-yl)-phenol (referred to herein as "DPTIP" and also as "DPTIP"), a small molecule inhibitor of neutral sphingomyelinase 2 (nSMase2), for the treatment of neurodegenerative and oncologic diseases.

More particularly, unbiased screening of the National Center for Advancing Chemical Sciences (NCATS) chemical library using a human neutral sphingomyelinase assay identified DPTIP (2,6-dimethoxy-4-(5-phenyl-4-thiophen-2-yl-1H-imidazol-2-yl)-Phenol (DPTIP)) as potent inhibitor of nSMase2 ($IC_{50}$=30 nM). DPTIP is a non-competitive inhibitor with respect to sphingomyelin, inhibits exosome release both in vitro and in vivo, is metabolically stable, and penetrates the brain ($AUC_{brain}/AUC_{plasma}$=0.26).

Until the present disclosure, there have been no drug-like inhibitors of human neutral sphingomyelinase. The most widely used inhibitor, GW4869, was identified from an early screen using rat neutral sphingomyelinase over 15 years ago (2002 J Biol Chem 277, 41128). GW4869 has a high molecular weight (MW 577), is a weak nSMase2 inhibitor ($IC_{50}$=1 µM), exhibits poor solubility (solubility in DMSO is 0.2 mg/ml) and consequently has very limited ability to serve as pharmacological tool or as starting point for clinical development. In contrast, after developing a new human nSMase2 assay and screening the NCATS chemical library (350,000 compounds), DPTIP (MW 378) has been identified as a potent ($IC_{50}$=30 nM), drug-like nSMase2 inhibitor.

It is thought that DPTIP is the most potent and drug-like nSMase2 inhibitor identified to date. Based upon genetic and pharmacological inhibition studies of nSMase2, DPTIP will have broad utility in neurodegenerative and oncologic diseases where abnormal exosome secretion is presumed pathogenic.

Representative therapeutic utilities of nSMase2 inhibition include, but are not limited to Alzheimer's Disease (AD), 2015 Nat Neurosci 18, 1584; 2016 J Neurosci 8653; 2014 Neurobiol Aging 1792, 2012 Progress in Lipid Research 51, 378; 2010 J Neurosci 30, 12676; Multiple Sclerosis (MS), 2010 Neuromol Med 12, 351; 2009 Journal of the Neurological Sciences 278, 5; Amyotrophic Lateral Sclerosis (ALS), 2002 Ann Neurol 52, 448; HIV-Associated Neurocognitive Disorders (HAND)—2004 J Neurosci 24, 9531; 2004 Ann Neurol 55, 257; and Cancer—2013 J Biol Chem 288, 10849; 2012; Neurochem Res 37, 1137). More generally, inhibition of nSMase2 also inhibits exosome biosynthesis, 2008 Science 1244; 2017 J Extracellular Vesicles 1378056.

Accordingly, in some embodiments, the presently disclosed subject matter provides a method for treating one or more diseases associated with neutral sphingomyelinase 2 (nSMase2) in a subject in need of treatment thereof, the method comprising administering to the subject a therapeutically effective amount of 2,6-dimethoxy-4-(5-phenyl-4-thiophen-2-yl-1-imidazol-2-yl)-phenol (DPTIP) or a pharmaceutically acceptable salt thereof. In certain embodiments, the administration of an effective amount of DPTIP to the subject decreases or inhibits the (nSMase2) activity or expression in the subject. In particular embodiments, the one or more diseases associated with neutral sphingomyelinase 2 (nSMase2) results in an elevated level of ceramide in the subject.

In some embodiments, the presently disclosed subject matter provides a method for treating a neurodegenerative disease in a subject in need of treatment thereof, the method comprising administering to the subject a therapeutically effective amount of DPTIP or a pharmaceutically effective salt thereof.

By "neurodegenerative disease, disorder, or condition" is meant a disease, disorder, or condition (including a neuropathy) associated with degeneration or dysfunction of neurons or other neural cells, such as retinal ganglion cells. A neurodegenerative disease, disorder, or condition can be any disease, disorder, or condition in which decreased function or dysfunction of neurons, or loss or neurons or other neural cells, can occur.

Such diseases, disorders, or conditions include, but are not limited to, glaucoma, and neurodegenerative diseases, disorders, or conditions of the nervous systems, such as or associated with amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, Alzheimer's disease (AD), Huntington's disease, Parkinson's disease, Parkinson's-plus diseases, multiple system atrophy, progressive supranuclear palsy, corticobasal degeneration, dementia with Lewy bodies, frontotemporal dementia, demyelinating diseases, Guillain-Barre syndrome, multiple sclerosis (MS), Charcot-Marie-Tooth disease, prion diseases, Creutzfeldt-Jakob disease, Gerstmann-Straussler-Scheinker syndrome (GSS), fatal familial insomnia (FFI), bovine spongiform encephalopathy (BSE), Pick's disease, epilepsy, HIV-associated neurocognitive disorders (HAND), and AIDS demential complex.

Other neurodegenerative diseases, disorders, or conditions of the nervous systems, such as or associated with alcoholism, Alexander's disease, Alper's disease, ataxia telangiectasia, Batten disease (also known as Spielmeyer-Vogt-Sjogren-Batten disease), Canavan disease, Cockayne syndrome, diabetic neuropathy, frontotemporal lobar degeneration, HIV-associated dementia, Kennedy's disease, Krabbe's disease, neuroborreliosis, Machado-Joseph disease (Spinocerebellar ataxia type 3), wet or dry macular degeneration, Niemann Pick disease, Pelizaeus-Merzbacher Disease, photoreceptor degenerative diseases, such as retinitis pigmentosa and associated diseases, Refsum's disease, Sandhoff's disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), Steele-Richardson-Olszewski disease, and tabes dorsalis.

In particular embodiments, the neurodegenerative disease is selected from the group consisting of Alzheimer's disease (AD), multiple sclerosis (MS), amyotrophic lateral sclerosis (ALS), and HIV-associated neurocognitive disorders (HAND).

In some embodiments, the presently disclosed subject matter provides a method for treating a cancer in a subject in need of treatment thereof, the method comprising administering to the subject a therapeutically effective amount of DPTIP or a pharmaceutically effective salt thereof.

As used herein, a "cancer" in a patient refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. A "tumor," as used herein, refers to all neoplastic cell growth and proliferation, whether malignant or benign, and all precancerous and cancerous cells and tissues. A "solid tumor," as used herein, is an abnormal mass of tissue that generally does not contain cysts or liquid areas. A solid tumor may be in the brain, colon, breasts, prostate, liver, kidneys, lungs, esophagus, head and neck, ovaries, cervix, stomach, colon, rectum, bladder, uterus, testes, and pancreas, as non-limiting examples. In some embodiments, the solid tumor regresses or its growth is slowed or arrested after the solid tumor is treated with the presently disclosed methods. In other embodiments, the solid tumor is malignant. In some embodiments, the cancer comprises Stage 0 cancer. In some embodiments, the cancer comprises Stage I cancer. In some embodiments, the cancer comprises Stage II cancer. In some embodiments, the cancer comprises Stage III cancer. In some embodiments, the cancer comprises Stage IV cancer. In some embodiments, the cancer is refractory and/or metastatic. For example, the cancer may be refractory to treatment with radiotherapy, chemotherapy or monotreatment with immunotherapy. Cancer as used herein includes newly diagnosed or recurrent cancers, including without limitation, acute lymphoblastic leukemia, acute myelogenous leukemia, advanced soft tissue sarcoma, brain cancer, metastatic or aggressive breast cancer, breast carcinoma, bronchogenic carcinoma, choriocarcinoma, chronic myelocytic leukemia, colon carcinoma, colorectal carcinoma, Ewing's sarcoma, gastrointestinal tract carcinoma, glioma, glioblastoma multiforme, head and neck squamous cell carcinoma, hepatocellular carcinoma, Hodgkin's disease, intracranial ependymoblastoma, large bowel cancer, leukemia, liver cancer, lung carcinoma, Lewis lung carcinoma, lymphoma, malignant fibrous histiocytoma, a mammary tumor, melanoma, mesothelioma, neuroblastoma, osteosarcoma, ovarian cancer, pancreatic cancer, a pontine tumor, premenopausal breast cancer, prostate cancer, rhabdomyosarcoma, reticulum cell sarcoma, sarcoma, small cell lung cancer, a solid tumor, stomach cancer, testicular cancer, and uterine carcinoma.

In some embodiments, the cancer is acute leukemia. In some embodiments, the cancer is acute lymphoblastic leukemia. In some embodiments, the cancer is acute myelogenous leukemia. In some embodiments, the cancer is advanced soft tissue sarcoma. In some embodiments, the cancer is a brain cancer. In some embodiments, the cancer is breast cancer (e.g., metastatic or aggressive breast cancer). In some embodiments, the cancer is breast carcinoma. In some embodiments, the cancer is bronchogenic carcinoma. In some embodiments, the cancer is choriocarcinoma. In some embodiments, the cancer is chronic myelocytic leukemia. In some embodiments, the cancer is a colon carcinoma (e.g., adenocarcinoma). In some embodiments, the cancer is colorectal cancer (e.g., colorectal carcinoma). In some embodiments, the cancer is Ewing's sarcoma. In some embodiments, the cancer is gastrointestinal tract carcinoma. In some embodiments, the cancer is a glioma. In some embodiments, the cancer is glioblastoma multiforme. In some embodiments, the cancer is head and neck squamous cell carcinoma. In some embodiments, the cancer is hepatocellular carcinoma. In some embodiments, the cancer is Hodgkin's disease. In some embodiments, the cancer is intracranial ependymoblastoma. In some embodiments, the cancer is large bowel cancer. In some embodiments, the cancer is leukemia. In some embodiments, the cancer is liver cancer. In some embodiments, the cancer is lung cancer (e.g., lung carcinoma). In some embodiments, the cancer is Lewis lung carcinoma. In some embodiments, the cancer is lymphoma. In some embodiments, the cancer is malignant fibrous histiocytoma. In some embodiments, the cancer comprises a mammary tumor. In some embodiments, the cancer is melanoma. In some embodiments, the cancer is mesothelioma. In some embodiments, the cancer is neuroblastoma. In some embodiments, the cancer is osteosarcoma. In some embodiments, the cancer is ovarian cancer. In some embodiments, the cancer is pancreatic cancer. In some embodiments, the cancer comprises a pontine tumor. In some embodiments, the cancer is premenopausal breast cancer. In some embodiments, the cancer is prostate cancer. In some embodiments, the cancer is rhabdomyosarcoma. In some embodiments, the cancer is reticulum cell sarcoma. In some embodiments, the cancer is sarcoma. In some embodiments, the cancer is small cell lung cancer. In some embodiments, the cancer comprises a solid tumor. In some embodiments, the cancer is stomach cancer. In some embodiments, the cancer is testicular cancer. In some embodiments, the cancer is uterine carcinoma.

In some embodiments, the presently disclosed subject matter provides a method for treating cardiac disease in a subject in need of treatment thereof, the method comprising administering to the subject a therapeutically effective amount of DPTIP or a pharmaceutically effective salt thereof. In particular embodiments, the cardiac disease is a myocardial disease involving myocyte hypertrophy, fibroblast-derived cardiac hypertrophy, heart failure, heart hypertrophy, diastolic and/or systolic ventricular dysfunction and/or a cardiovascular disease involving fibrosis, aortic stenosis, atrial fibrillation, genetic forms of cardiomyopathy, cardiac storage diseases and/or fabry disease.

In other embodiments, the presently disclosed subject matter provides a method for inhibiting neutral sphingomyelinase 2 (nSMase2), the method comprising contacting a cell comprising nSMase2 with an amount of 2,6-dimethoxy-4-(5-phenyl-4-thiophen-2-yl-1H-imidazol-2-yl)-phenol (DPTIP) or a pharmaceutically acceptable salt thereof.

In yet other embodiments, the presently disclosed subject matter provides a method for inhibiting exosome biosynthesis, the method comprising contacting a cell with an amount of 2,6-dimethoxy-4-(5-phenyl-4-thiophen-2-yl-1H-imidazol-2-yl)-phenol (DPTIP) or a pharmaceutically acceptable salt thereof.

In even yet other embodiments, the presently disclosed subject matter provides a method for inhibiting ceramide biosynthesis, the method comprising contacting a cell with an amount of 2,6-dimethoxy-4-(5-phenyl-4-thiophen-2-yl-1H-imidazol-2-yl)-phenol (DPTIP) or a pharmaceutically acceptable salt thereof.

In other embodiments, the presently disclosed subject matter provides for the use of 2,6-dimethoxy-4-(5-phenyl-4-thiophen-2-yl-1H-imidazol-2-yl)-phenol (DPTIP) for the production of a medicament for treating one or more diseases associated with neutral sphingomyelinase 2 (nSMase2).

As used herein, the term "inhibit," and grammatical derivations thereof, refers to the ability of a presently disclosed compound, e.g., a presently disclosed compound of DPTIP, to block, partially block, interfere, decrease, or reduce the growth of bacteria or a bacterial infection. Thus, one of ordinary skill in the art would appreciate that the term "inhibit" encompasses a complete and/or partial decrease in the growth of bacteria or a bacterial infection, e.g., a decrease by at least 10%, in some embodiments, a decrease by at least 20%, 30%, 50%, 75%, 95%, 98%, and up to and including 100%.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

The term "combination" is used in its broadest sense and means that a subject is administered at least two agents, more particularly DPTIP and at least one other active agent. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, DPTIP can be administered alone or in combination with adjuvants that enhance stability of DPTIP, alone or in combination with one or more active agents, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of DPTIP and at least one additional therapeutic agent can be varied so long as the beneficial effects of the combination of these agents are achieved. Accordingly, the phrase "in combination with" refers to the administration of DPTIP and at least one additional therapeutic agent either simultaneously, sequentially, or a combination thereof. Therefore, a subject administered a combination of DPTIP and at least one additional therapeutic agent can receive DPTIP and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where DPTIP and at least one additional therapeutic agent are administered simultaneously, they can be administered to the subject as separate pharmaceutical compositions, each comprising either DPTIP or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of DPTIP and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A + Q_b/Q_B = \text{Synergy Index(SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

D. Pharmaceutical Compositions and Administration

In another aspect, the present disclosure provides a pharmaceutical composition including DPTIP alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments±50%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

High Throughput Screening Identifies a Potent, Brain Penetrant Neutral Sphingomyelinase 2 Inhibitor that Blocks Exosome Release In Vitro and In Vivo

1.1 Overview

To find novel nSMase2 inhibitor scaffolds, a high throughput screening campaign of more than 350,000 compounds was carried out using a cell-free enzymatic assay with human recombinant nSMase2. Several chemically distinct hits were identified including 2,6-Dimethoxy-4-(5-Phenyl-4-Thiophen-2-yl-1H-Imidazol-2-yl)-Phenol (DPTIP), a non-competitive inhibitor with an $IC_{50}$=40 nM, making it the most potent nSMase2 inhibitor reported to date. DPTIP was found to be metabolically stable in mouse and human liver microsomes with a good pharmacokinetic profile in mice ($C_{max}$=11.6±0.5 nmol/mL; $T_{max}$=0.5 h; AUC=10±1 nmol/mL*h), and with significant brain penetration (brain $AUC_{0-\infty}$/plasma $AUC_{0-\infty}$=0.26). DPTIP dose-dependently inhibited exosome release in primary mouse glial cultures with an $EC_{50}$=3 µM, while its closely related, but nSMase inactive des-hydroxyl analog, had no effect. When dosed in mice engineered with GFP-labeled glial cells, DPTIP (10 mg/kg IP) robustly inhibited IL1-β-induced release of brain-derived exosomes into plasma by 70+SEM %. In sum, the presently disclosed subject matter identifies a potent brain penetrant nSMase2 inhibitor that blocks exosome release in vitro and in vivo.

1.2 Background

Post mortem brains from Alzheimer's disease (AD) patients exhibit an abnormal elevation of endogenous ceramide (Filippov, et al., 2012; Mielke, et al., 2010; Satoi, et al., 2005) an integral component of exosomes (Trajkovic, et al., 2008) and a product of sphingomyelin hydrolysis catalyzed by neutral sphingomyelinase 2 (nSMase2). Recent preclinical studies using the 5XFAD mouse model of AD showed that exosomes stimulate aggregation of Aβ both in vitro and in vivo and that pharmacological inhibition of nSMase2 resulted in brain and serum exosome reduction, lower brain ceramide and lower Aβ load (Dinkins, et al., 2014). Additional studies using the same model showed that ceramide-enriched exosomes exacerbated AD pathology and cognitive deficits while genetic nSMase2 deficiency ameliorated AD pathology and improved cognition (Dinkins, et al., 2016).

In an independent study using two AD mouse models of tau propagation, exosomes were shown to be involved in tau propagation and both genetic deletion and pharmacological inhibition of nSMase2 prevented exosome manufacturing and subsequent tau propagation (Asai, et al., 2015). While production of ceramide through nSMase2 is part of normal brain functioning (Wheeler, et al., 2009), chronic upregulation of the enzyme has been implicated in the pathogenesis of various neurodegenerative diseases including AD (Filippov, et al., 2012; Satoi, et al., 2005; Alessenko, et al., 2004; Marks, et al., 2008; Mielke, et al., Alzheimers Dement, 2010; Wang, et al., 2008), HIV-associated neurocognitive disorders (HAND) (Jana, et al., 2004; Haughey, et al., 2004), multiple sclerosis (MS) (Jana, et al., 2010) and amyotrophic lateral sclerosis (ALS) (Cutler, et al., 2002). NSMase2 is predominantly expressed in brain and it is this isoform, rather than nSMase 1 or 3, that is implicated in neurodegenerative disease (Wu, et al., 2010; Horres, et al., 2012). Taken together, nSMase2 has emerged as an important player in AD etiology, and clinical and preclinical evidence provide a compelling rationale for the use of nSMase2 inhibitors for the treatment of AD.

Unfortunately, currently available nSMase2 inhibitors have low potency ($IC_{50}$'s in the µM level), poor solubility, and limited brain penetration. GW4869 (Luberto, et al., 2002), the most widely used inhibitor, has low inhibitory potency ($IC_{50}$=1 µM) and very poor solubility (<1 µg/mL in aqueous buffer), which has limited its clinical potential. Cambinol, an inhibitor identified previously based on a pilot screen of commercially available small chemical libraries (Figuero-Losada, et al., 2015) showed better solubility, but it was metabolically unstable and exhibited a poor in vivo pharmacokinetic profile. Chemistry efforts to improve cambinol's potency ($IC_{50}$=7 µM) and stability were unsuccessful. The presently disclosed subject matter provides a high throughput screening (HTS) campaign that identified a potent inhibitor of nSMase2, with a good pharmacokinetic profile including brain penetration, which was capable of blocking exosome release both in vitro and in vivo.

1.3 Results

1.3.1 Development of a 1536-Well Cell-Free Human Recombinant nSMase2 Enzyme Activity Assay Human nSMase2 catalyzes the hydrolysis of sphingomyelin (SM) to phosphorylcholine and ceramide. The Amplex Red system was used to monitor nSMase2 activity (Figuero-Losada, et al., 2015). In this reaction, one of the products, phosphorylcholine, is stoichiometrically converted through a series of enzyme-coupled reactions to fluorescent resorufin, so that fluorescence signal is directly proportional to nSMase2 activity (FIG. 1A). The components of the coupling system were always added along with SM (see Methods, section 1.3.10 herein below). An enzymatic assay protocol was developed in 1536-well format for implementation in HTS. Several parameters were optimized through the measurement of the fluorescence signal. Fluorescence signal increased with longer time of incubation (15-150 min) and nSMase2 concentration (0.03 to 0.5 µg protein/mL) at a constant SM concentration (20 µM) (FIG. 1B). Similarly, fluorescence signal increased with longer time of incubation (15-150 min) and increasing SM concentrations (5-40 µM) at a constant enzyme concentration (0.063 µg protein/mL) (FIG. 1C). Based on these results, 0.1 µg protein/µL human nSMase2 cell lysate, 20 µM SM in a total volume of 4 µL and 2 h incubation at 37° C. were selected to assess assay performance in HTS format, including Z'-factor determination. Under these conditions, reaction rate was linear with a robust fluorescence signal of approximately 2500 relative fluorescent units (RFU). Cambinol was used as inhibitor control (Figuero-Losada, et al., 2015); it was preincubated with human nSMase2 for 15 min prior to addition of SM. Final DMSO concentration was 0.57%. The assay exhibited signal/background=21 and Z'=0.8 which was optimal for the HTS campaign (FIG. 1D). Dose response of inhibition by cambinol and GW4869 also was evaluated to determine variability in $IC_{50}$ values from plate to plate. GW4869 was insoluble in DMSO and appeared as a yellow pellet at the 3 highest concentrations so it was excluded as control. Cambinol's average $IC_{50}$ from 4 independent determinations was 27±1 µM (FIG. 1E). The final stage of validation of the assay for HTS was the screening of the Library of Pharmacologically Active Compounds (LOPAC) in 1536-well plates using the same assay conditions outlined in FIG. 1D at four different inhibitor concentrations (0.4 µM, 2 µM, 11 µM and 57 µM). Overall, the sample field was even, there were no plate positional effects and hits increased as the concentration increased.

1.3.2 HTS Campaign and Data Analysis of Hits LED to the Identification of DPTIP as a Potent nSMase2 Inhibitor Following assay validation, 365,000 compounds were screened from the Molecular Libraries Small Molecule Repository (MLSMR) and 2816 compounds were screened from the NCGC pharmaceutical collection (NPC) library for human nSMase2 inhibitors. Compounds were screened at 4 concentrations: 1.1 µM, 11 µM, 57 µM and 114 µM. Cambinol (full does response in each plate) was used as positive control. After eliminating promiscuous compounds, 1990 compounds that had maximal inhibitory responses >50% at the highest concentration tested and robust curve response classes (CRC) (Inglese, et al., 2006) were selected for re-testing in the same human nSMase2 activity assay and counter screen. The purpose of the counter screen was to identify false positives, i.e., compounds that inhibited the enzyme-coupled reactions; it was carried out in the absence of human nSMase2 and SM and using phosphorylcholine as substrate. Out of the 1990 compounds, 1782 (90%) were confirmed in the 7 dose-response hnSMase2 confirmatory assay, but most (1718; 86%) were found to be false positives in the counter screen, resulting in 64 bona fide nSMase2 inhibitors. The difference between potency and response in the counter screen also was considered to select 156 additional hits that showed robust inhibition of the overall reaction, but were weakly active in the counter screen. There were a total of 220 compounds for follow-up confirmation (FIG. 2A). Out of the 220 compounds, 7 compounds exhibited dose responses with $IC_{50}$<10 µM that also were inactive in the counter assay (FIG. 2B).

1.3.3 DPTIP is the Most Potent nSMase2 Inhibitor Reported to Date

Filtering of the HTS hits as outlined above resulted in the identification of DPTIP as the most promising compound in terms of potency and chemical optimization feasibility. The $IC_{50}$ for DPTIP using an extended inhibitor concentration range (10 pM-100 µM) was 30 nM (FIG. 3A). This $IC_{50}$ is approximately 30- and 160-fold more potent than the prototype inhibitors GW4869 (1 µM) (Luberto, et al., 2002) and cambinol (5 µM), respectively. It is thought that DPTIP is the first nSMase2 inhibitor described with nanomolar level potency. Because DPTIP contains a hydroxyl group, which could be a metabolic liability in vivo (FIG. 3A), the importance of this group for inhibitory activity was investigated. Accordingly, the des-hydroxyl analog of DPTIP (FIG. 3B) was synthesized and was shown to be inactive against human nSMase2 ($IC_{50}$>100 µM) (FIG. 3B). These results demonstrate the importance of the hydroxyl group for inhibition and also provided a structurally similar, yet inactive DPTIP analog, to use as a comparison compound in subsequent pharmacological assays to show nSMase specificity.

1.3.4 DPTIP Exhibited Non-Competitive Mode of Inhibition and Showed Selectivity for nSMase2 Versus Related Enzymes DPTIP exhibited the hallmarks of noncompetitive inhibition; when rate of reaction with respect to SM concentration was monitored at increasing inhibitor concentrations there was a decrease in maximal ($V_{max}$) while the Michaelis constant ($K_m$) was unchanged (FIG. 3C). $V_{max}$ and $K_m$ for each data set at a given inhibitor concentration were obtained from non-linear regression fits to Michaelis-Menten kinetics (FIG. 3C).

DPTIP did not inhibit members of two related enzyme families including alkaline phosphatase ($IC_{50}$>100 µM in counter screen), a phosphomonoesterase, or, in a separate selectivity study using a standard protocol (Li, et al., 2010), acid sphingomyelinase ($IC_{50}$>100 µM), a phosphodiesterase closely related to nSMase2 (results not shown). Inhibitor selectivity with respect to enzymes from related families is consistent with the noncompetitive mode of inhibition, as DPTIP is likely acting at a site other than the catalytic site. Additional data also indicate that DPTIP exhibits specificity for nSMase2; DPTIP has been screened in 759 bioassays assays at NCATS and only weak activity (2-50 µM) was observed in 19 (0.025%) of these assays (pubchem.ncbi.nlm.nih.gov/compound/5446044#section=BioAssay-Results).

1.3.5 DPTIP Showed Metabolic Stability in Mouse and Human Liver Microsomes

One potential liability when using chemical probes in vivo is lack of metabolic stability which structurally inactivates the compound before it can reach its molecular target. DPTIP was evaluated for metabolic stability using human and mouse liver microsomes as have been previously described (Rais, et al., 2016). Percent of drug remaining over time was determined by liquid chromatography-tandem mass spectrometry analysis (LC/MS/MS). In the presence of NADPH, DPTIP remained intact (100% remaining at 1 h) in both mouse and human liver microsomes (FIG. 4A) indicating that the compound is not affected by CYP-450-mediated metabolism. These in vitro results indicate DPTIP does not have major liver metabolic liabilities that would preclude its use as an in vivo probe.

1.3.6 DPTIP Exhibited Plasma Exposure and Brain Penetration after Systemic Dosing in Mice In the next set of experiments, the in vivo pharmacokinetic profile of systemically administered DPTIP was evaluated. Mice were given DPTIP (10 mg/kg IP) and plasma and brain levels of DPTIP were measured at 0.25, 0.50, 1, 2, 4 and 6 h post dose (n=3 per time point). DPTIP peak concentration in both plasma and brain at 0.5 h ($C_{max}$ plasma=11.6±0.5 µM; $C_{max}$ brain=2.5 µM). The $AUC_{0-\infty}$ of DPTIP in plasma and brain was 10±1 and 2.6±0.5 µM*h respectively, resulting in an $AUC_{brain}/AUC_{plasma}$=0.26 (FIG. 4B and FIG. 4C). Brain levels of DPTIP exceeded its $IC_{50}$ for inhibition of nSMase for up to 4 hrs following 10 mg/kg systemic dosing (FIG. 4B).

1.3.7 DPTIP Inhibited Exosome Release from Primary Astrocytes Whereas its Inactive Des-Hydroxyl Analog had No Effect Independent laboratories have shown that both pharmacological and genetic inhibition of nSMase2 results in inhibition of exosome secretion from glial cells leading to blockade of Aβ plaque aggregation (Dinkins, et al., 2014; Dinkins, et al., 2016) and tau propagation (Asai, et al., 2015). Consequently, DPTIP was evaluated for its ability to inhibit exosome release from primary glial cells in vitro. Specifically, mouse primary astrocytes were activated by FBS withdrawal as previously described (Dickens, et al., 2017) and treated with DPTIP or its closely related inactive des-hydroxyl analog (FIG. 5A) at a dose range of concentrations (0.03-30 µM) using DMSO (0.02%) as vehicle control. Two hours after treatment, exosomes were isolated from the media and quantified (see Methods, section 1.3.10 herein below). The mean concentration of exosomes (EVs/mL±SEM) was calculated from 4 replicate experiments. DPTIP inhibited exosome release from astrocytes in a dose dependent manner (FIG. 5A) with an $EC_{50}$ of approximately 3 µM. In contrast, its closely related inactive analog had no effect on exosome release suggesting DPTIP inhibits exosome release via nSMAse2 inhibition.

Figure 5D:
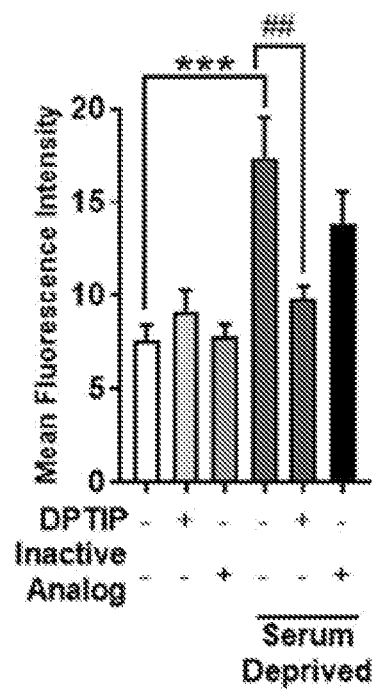

The activation status of (+/−) serum-deprived astrocytes after DPTIP treatment also was determined. Rat primary astrocytes were treated with DPTIP (10 µM) or inactive analog for two hours along with (+/−) serum deprivation-induced stress. Cells were fixed and immunofluorescence labeling for GFAP was performed. DPTIP and inactive analog without serum starvation did not change GFAP levels (FIG. 5C and FIG. 5D). Serum deprivation resulted in activation of astrocytes as evidenced by increase in GFAP fluorescence intensity compared to non-treated controls. Treatment with DPTIP prevented astrocyte activation in response to serum starvation, while the inactive analog failed to prevent astrocyte activation (FIG. 5C and FIG. 5D).

1.3.8 DPTIP Inhibited Biomarkers of Brain Inflammation In Vivo Whereas its Inactive Des-Hydroxyl Analog, DPT, had No Effect Given DPTIP's brain penetration in mice and its ability to inhibit exosome release in vitro, the ability of DPTIP to ameliorate EV release from astrocytes, cytokine regulation in liver and neutrophil migration into brain in an in vivo mouse model of brain inflammation was evaluated. As has been previously shown (Dickens, et al., 2017; McCluskey, et al., 2008), striatal injection of IL-1β in mice expressing GFAP-GFP in astroglia (see Methods, section 1.3.10 herein below) triggers a release of GFP-labelled EVs that rapidly entered into plasma, resulting in liver and peripheral immune cell migration into brain (Dickens, et al., 2017).

Mice were dosed (10 mg/kg IP, DPTIP or inactive analog) 0.5 h prior to IL-1β striatal injection. At this dose, brain concentrations of DPTIP are above its $IC_{50}$ for nSMase2 inhibition for at least 4 h after compound administration (FIG. 4C). There were two groups of mice: the first group was sacrificed 2 h after IL-1β administration by heart puncture, and GFP-labeled circulating EVs were measured with liver cytokines. Mice in the second group were dosed a second time with DPTIP or inactive analog at 12 h and sacrificed at 24 h after IL-1β administration to measure brain neutrophils (FIG. 6A). Counting of astrocyte-released EV (GFP+) from blood and liver cytokine analysis was conducted by single injection of DPTIP. Although release of EVs from astrocytes can be initiated immediately after intracranial injection of IL-1β, infiltration of neutrophils in brain parenchyma occurred 12 h-24 h after the IL-1β injection. Since the pharmacokinetic profiles of DPTIP in plasma and brain following 10 mg/kg IP dose showed that brain levels of DPTIP exceeded its $IC_{50}$ for nSMase2 for only 4 h post dose, DPTIP was administered twice after IL-1β injection to ensure inhibition of nSMase2 was sustained during the experiment. When mice were dosed with DPTIP, number of astrocyte-derived EVs was reduced by 51±13% 2 h post IL-1β administration (FIG. 6B). Western blot analysis using the isolated exosomal fraction confirmed the presence of CD63 (transmembrane protein), TSG101 (cytosolic protein) and Flotilin-1 (lipid raft associated protein), commonly used EV markers (Lotvall, et al., 2014; von der Malsburg, et al., 2011). The GFP signal was an indication that these EVs originated in brain, (Dickens, et al., 2017) while lack of mitofilin and α-actinin signals indicated the vesicles were not of mitochondrial (von der Malsburg, et al., 2011) or cytoskeletal (Sjoblom, et al., 2008) origin, respectively (FIG. 6B). Upregulation of liver cytokines upon IL-1β treatment was inhibited by DPTIP (FIG. 6C). Neutrophils, as measured by immunohistochemistry of coronal brain sections using LY6b antibody, showed reduced staining in sections from animals treated with DPTIP compared to IL-1β-treated animals (FIG. 6D); corresponding quantification showed neutrophil migration into brain was reduced by 80±23% compared to IL-1β-treated animals (FIG. 6E). Administration of the closely related inactive analog, had no statistically significant effect on IL-1β-induced EV release (FIG. 6B). The effects of the inactive des-hydroxyl DPTIP on production of TNF-α and IL-6 were marginal and not statistically significant. Although the magnitude of reduction in CCL2 production by the inactive analog was high, the data were variable and also not statistically significant (FIG. 6C). Finally, des-hydroxyl DPTIP had no effect on neutrophil migration (FIG. 6D, FIG. 6E). Results with the inactive analog were consistent with the suggestion that DPTIP effects occur through nSMase2 inhibition. Importantly, these results agree with previous findings that co-injection of IL-1β with nSMase2 inhibition (either GW4869, altenusin, lentivirus targeting astrocytic nSMase2, or using nSMase2 KO mice) suppresses neutrophil infiltration into brain parenchyma (Dickens, et al., 2017). The same studies also indicated that nSMase2 inhibition suppressed activation of astrocytes and microglia (Dickens, et al., 2017). Within the present study, efforts were focused on astrocytes because of the intimate association of these cells with the blood-brain barrier (BBB), and because in a previous study nSMase2 expression was knocked down selectively in astrocytes and this was shown to inhibit the release of astrocyte-derived EVs (ADEVs) and prevent the liver cytokine response and leukocyte trafficking into brain following parenchymal injection of IL-1beta (Dickens, et al., 2017).

Although it remains possible that neuronal or microglial-derived EV are also affected by nSMase2 inhibition, these earlier findings suggest that ADEVs are a major source of brain EVs that regulate the peripheral response to CNS injury. Future studies will include the use of neuronal and microglial derived EVs. The exact mechanism of serum deprivation-induced EV release is not known. Serum deprivation is known to produce a stress response that stimulates secretory pathways in astrocytes (Shin, et al., 1996). Additionally, nutrient deprivation has been shown to cause accumulation of ceramides in astrocytes, likely due to a stress response activation of nSMase2 (Gu, et al., 2013). Nutrient starvation has been reported to increase nSMase2 activity and induce its expression in other cell types (Back, et al., 2018). Serum deprivation induced EV release observed in our experiments may therefore be the result of nSMase2 activation in response to nutrient deprivation stress.

A schematic illustration of the in vivo experiment are shown in FIG. 7, which are consistent with the data detailed above, as well as previous literature. In brief, striatal IL-1β injection activates the IL-1β receptor on the plasma membrane of astrocytes that in turn activates nSMase2 enzymatic activity to catalyze the hydrolysis of sphingomyelin to produce ceramide (Mathias, et al., 1993). Ceramide is used to manufacture intracellular vesicles (IVs) (Trajkovic, et al., 2008) that are released from astrocytes as EVs and migrate into plasma where they induce a peripheral acute cytokine response, mainly in liver, and prime immune cells to transmigrate to the brain (Dickens, et al., 2017). In the presence of DPTIP, inhibition of nSMase2 prevents ceramide production, EV formation and secretion (FIG. 6B) cytokine upregulation (FIG. 6C) and neutrophil migration (FIG. 6D).

1.3.9 Summary

In summary, DPTIP is the most potent nSMase2 inhibitor identified to date ($IC_{50}$ 30 nM), exhibits selectivity, is metabolically stable and brain penetrant. DPTIP is an inhibitor of EV release in primary glial cells and in vivo. In addition, biomarkers that have been associated with EV release from brain, including cytokine upregulation and immune cell migration to brain, also were inhibited by DPTIP. The des hydroxyl inactive analog of DPTIP did not inhibit EV release in vitro and had no effect on IL-1β-induced cytokine regulation or neutrophil migration to brain in vivo. DPTIP is a considerable improvement over other nSMase2 inhibitors identified to date. It can be used as a probe in animal models of disease associated with EV dysregulation and it contains a structural scaffold that is actively being optimized for clinical translation.

1.3.10 Methods

1.3.10.1 Expression of Human nSMase2

Full length human nSMase2 cDNA with a C-terminal Flag tag cloned into a pCMV6-Entry expression vector (Origene) was transfected into HEK293 cells using lipofectamine 2000 (Life Technologies). Selection of transfected cells was carried out for two weeks with 500 µg/mL G418 in EMEM containing 10% FBS (ATCC) and 2 mM glutamine (Life Technologies). Expression of human nSMase2 was confirmed by Western-blot analysis using an antibody specific against nSMase2 (R&D) diluted to 0.4 µg/mL in Tris-buffered saline with 0.1% Tween 20 and 5% bovine serum albumin. Cells expressing human nSMase2 were grown to confluency in 150-mm dishes, washed twice with cold PBS and harvested using a cell scraper in lysis buffer pH 7.5, Tris-HCl 100 mM, 1 mM EDTA, 100 mM sucrose, 100 µM PMSF, 1× protease inhibitor cocktail III (Calbiochem), 1 mL per dish. Cell lysis was achieved by sonicating 3 times on ice for 30 sec. Protein concentration was determined using the bicinchoninic acid (BCA) assay. Aliquots of cell lysate were snap frozen and stored at −80° C. Activity of recombinant human nSMase2 from cell lysates remained stable for at least six months.

1.3.10.2 Fluorescence-Based nSMase2 Activity Assay in 1536-Well Format

Measurements of nSMase2 activity using fluorescence as readout was optimized for dose response quantitative HTS (qHTS). The assay was carried out in black solid bottom, medium binding, 1536-well plates (Greiner, 789176-F). Fluorescence response was optimized with respect to nSMase2 concentration, incubation time and SM concentration. Recombinant human nSMase2 preparations (2 µL) at various concentrations (0.03 to 0.5 µg protein/µL solution) were incubated with substrate/detection reaction mixture (2 µL) containing various concentrations of SM (5 to 40 µM), coupling enzymes (alkaline phosphatase 4 U/mL, choline oxidase 0.1 U/mL and horseradish peroxidase 0.1 U/mL) and Amplex Red® (50 µM). Hydrolysis of SM was carried out for different incubation times (15-160 min) at 37° C. in pH 7.4 Tris-HCl buffer 100 mM, containing 10 mM $MgCl_2$ and 0.2% Triton X-100. Phosphorylcholine made during the nSMase2-catalyzed reaction is dephosphorylated by alkaline phosphatase to produce choline, which in turn undergoes oxidation in the presence of choline oxidase to produce betaine and peroxide. Peroxide in the presence of horseradish peroxidase and Amplex Red generates fluorescent resorufin (Ex 525/Em 598). Resorufin was monitored with a Viewlux µHTS Microplate Imager (Perkin Elmer) at energy levels of 1,000 or 3,000 and exposure times of 1 sec or 2 sec.

Based on results of the different conditions outlined above, the HTS campaign was carried out using 0.1 µg protein/µL nSMase2 preparation, 20 µM SM and 2 h time of incubation. Control inhibitors or test compounds (23 nL) were added from various concentrations in DMSO solution into to the nSMase2 preparation and incubated for 15 min prior to the addition of substrate and enzyme-coupling detection reagents. Compounds were screened in 4 doses, starting at 57 µM, and doing 5-fold dilutions. A customized screening robot (Kalypsys) was used for the primary screen. A step-by step HTS assay protocol is given in FIG. 8. Inhibitors of nSMase2 were selected using compound dose response curve algorithms developed at NCGC to score actives, which assigns each tested compound a compound response class (CRC) number (Inglese, et al., 2006). This method classifies primary hits into different categories according to their potency ($IC_{50}$), magnitude of response (efficacy), quality of curve fitting (r2), and number of asymptotes. For example, CRC of −1.1 represents complete curve and high efficacy; CRC of −1.2 represents complete curve but partial efficacy. Compounds with CRCs of −1.1, −1.2, −2.1 and −2.2 were generally selected for confirmation and validation. Structural analysis of selected compounds was performed and promiscuous compounds were filtered out. A counter-assay to rule out compounds that inhibited the detection reaction was carried out in the absence of human nSMase2, and the reaction was initiated with addition of phosphorylcholine (alkaline phosphatase substrate), added at a final concentration of 2 µM. Compounds that showed inhibitory activity in the counter-assay assay were removed from further validation.

1.3.10.3 $IC_{50}$ Determination of Selected Compounds

Human nSMase2 (0.1 µg protein/µL) was added to a reaction mixture containing SM (20 µM), and detection reagents as indicated above and different compound concentrations in the 10 pM-100 pM range in a total volume of 100 µL (96-well format). Kinetic measurements were obtained from 2 h traces when the reaction was linear. Percent inhibition was obtained using the formula [(rate of change of fluorescence in the presence of inhibitor divided by rate of change of fluorescence in the absence of inhibitor)×100].

1.3.10.4 Synthesis and Characterization of DPT

The synthesis scheme for the synthesis of the negative analog DPT along with a corresponding HPLC chromatogram are shown in FIG. 9.

1-Phenyl-2-(thiophen-2-yl) ethane-1,2-dione (60 mg, 0.28 mmol), 3,5-dimethoxybenzaldehyde (55 mg, 0.33 mmol, 1.2 equiv) and ammonium acetate (214 mg, 2.77 mmol, 10 equiv) were heated together in acetic acid (3 mL) at 150° C. overnight. Acetic acid was removed in vacuo. The crude material was dissolved in EtOAc (20 mL), washed with water (20 mL) and brine (20 mL). The organic layer was dried over sodium sulfate and concentrated. The resulting material was purified by Biotage (eluent: 20-40% EtOAc/hexanes) to give 75 mg (75% yield) of 2-(3,5-dimethoxyphenyl)-4-phenyl-5-(thiophen-2-yl)-1H-imidazole (DPT) as a white solid. The chemical structure of DPT was characterized by 1H NMR data, HPLC, mass spectrometry, and melting point.

1H NMR (400 MHz, d6-DMSO): δ 3.81 (6H, s), 6.51 (1H, t, J=2.1 Hz), 6.97 (1H, dd, J=3.8 Hz, 5.1 Hz), 7.04 (1H, dd, J=1.3 Hz, 3.5 Hz), 7.23 (1H, d, J=2.3 Hz), 7.34 (1H, s), 7.37 (1H, dd, J=1.3 Hz, 5.1 Hz), 7.44 (1H, m), 7.51 (2H, t, J=7.3 Hz), 7.59-61 (2H, m), 12.74 (1H, s). M.P=239-241° C. MS calculated for C21H18N2O2S m/z: 362 [M+H]+; found 363.

1.3.10.5 Metabolic Stability

Metabolic stability assay was conducted in mouse or human liver microsomes as has been described previously (Rais, et al., 2016) with minor modifications. Briefly, the reaction was carried out using potassium phosphate buffer (100 mM, pH 7.4), in the presence of an NADPH regenerating system (compound final concentration was 1 µM; 0.2 mg/mL microsomes). Compound disappearance was monitored over time using a liquid chromatography and tandem mass spectrometry (LC/MS/MS) method. Chromatographic analysis was performed using an Accela ultra high-performance system consisting of an analytical pump and an autosampler coupled with a TSQ Vantage mass spectrometer (Thermo Fisher Scientific Inc., Waltham, Mass.). Separation of analyte was achieved at ambient temperature using Agilent Eclipse Plus column (100×2.1 mm i.d.) packed with a 1.8 µm C18 stationary phase. The mobile phase consisted of 0.1% formic acid in acetonitrile and 0.1% formic acid in water with gradient elution. The [M+H]+ ion transition of DPTIP (m/z 378.956→363.073, 200.055) and losartan (IS) (m/z 423.200→207.107, 180.880).

1.3.10.6 In Vivo Pharmacokinetics

Pharmacokinetic studies in mice were approved by the Animal Care and Use Committee at Johns Hopkins University. Male CD1 mice between 25 and 30 g were obtained from Harlan and maintained on a 12 h light-dark cycle with ad libitum access to food and water. Test compounds were dosed at 10 mg/kg IP at a dosing volume of 10 mL/kg. Blood and brain tissue were collected at 0.25, 0.5, 1, 2, 4 and 6 h post dose (n=3 per time point). Blood was obtained via cardiac puncture and plasma was harvested from blood by centrifugation at 3000×g for 15 min and stored at −80° C. Brain tissues were harvested following blood collection and immediately snap frozen in liquid nitrogen and stored at −80° C. until LC-MS analysis. Calibration standards were prepared using naïve mouse plasma or brain spiked with DPTIP. DPTIP standards and samples were extracted from plasma and brain by a one-step protein precipitation using acetonitrile (100% v/v) containing internal standard (losartan: 0.5 µM). The samples were vortex mixed for 30 secs and centrifuged at 10000×g for 10 min at 4° C. Fifty microliter of the supernatant was diluted with 50 µL water and transferred to a 250 µL polypropylene vial sealed with a Teflon cap and analyzed via LC/MS/MS as described above. Plasma concentrations (pmol/mL) as well as tissue concentrations (pmol/g) were determined and plots of mean plasma concentration versus time were constructed for PK analysis. Non-compartmental-analysis modules in Phoenix WinNonlin version 7.0 (Certara USA, Inc., Princeton, N.J.) were used to assess pharmacokinetic parameters including maximal concentration ($C_{max}$), time to $C_{max}$ ($T_{max}$), and area under the curve extrapolated to infinity ($AUC_{0-\infty}$).

1.3.10.7 Inhibition of Exosome Release from Primary Glial Cells

Potential inhibition of test compounds on EV release from primary astrocytes was carried out as previously described (Dickens et al., 2017). Briefly, rat primary astrocytes were seeded onto 6-well plates at a density of 20,000 cells/well. Twenty-four hours after seeding, astrocytes were washed with PBS and the medium changed to media without FBS. Absence of FBS mimics atrophic factor withdrawal stimulus causing EVs to be released from astrocytes via an nSMase2-dependent pathway. Astrocytes were then treated with test compounds at different concentrations: 0.03, 0.1, 0.3, 1, 3, and 10 µM. DMSO (0.02%) was used as control. Two hours after treatment, media was collected and centrifuged at 2700×g for 15 min at 4° C. The supernatant was collected and the number of EVs quantified using ZetaView Nanoparticle Tracker (Particle Metrix GmBH, Meerbusch, Germany) and the corresponding ZetaView software (8.03.04.01). Nanosphere size standard 100 nm (Thermo Scientific) was used to calibrate the instrument prior to sample readings. Instrument pre-acquisition parameters were set to 23° C., a sensitivity of 65, a frame rate of 30 frames per second (fps), a shutter speed of 100, and laser pulse duration equal to that of shutter duration. Post-acquisition parameters were set to a minimum brightness of 25, a maximum size of 200 pixels, and a minimum size of 10 pixels. For each sample 1 mL of the supernatant was injected into the sample-carrier cell and the particle count measured at 5 positions, with 2 cycles of reading per position. The cell was washed with PBS after every sample. Mean concentration of EVs/mL (±SEM) was calculated from 4 replicates.

1.3.10.8 Inhibition of Exosome Release In Vivo

All experimental protocols using vertebrate animals were reviewed by the Institutional Animal Care and Use Committee at Johns Hopkins University and are in accordance with the guidelines of the NIH guide for the care and use of laboratory animals. Striatal injections and EV measurements were performed as previously described by our group in adult (2-3 month) male GFAP-GFP mice (Jackson Laboratories) (McCluskey, et al., 2008; Dickens, et al., 2017). Mice were anesthetized with 3% Isoflourane (Baxter) in oxygen (Airgas), and placed in a stereotaxic frame (Stoelting Co.).

A small burr hole was drilled in the skull over the left striatum using a dental drill (Fine Scientific Tools). IL-1β (0.1 ng/3 µL) was injected (total volume of 3 µL) at the rate 0.5 µL/min via a pulled glass capillary tip diameter <50 µm (McCluskey, et al., 2008); using the stereotaxic coordinates: A/P+0.5; M/L−2; −3 D/V. Saline was used as a control. When DPTIP or its des-hydroxyl analog were used, they were given IP (10 mg/kg, 5% DMSO, 5% Tween-80 in saline) 30 min before IL-1β injection. Following infusion, the capillary was held in place for 5 min to allow for solution to diffuse into the tissue. Animals were sacrificed at 2 h by an overdose of anesthetic, and transcardially perfused with ice-cold saline containing heparin (20 µL per 100 ml, Sigma). Blood was collected via cardiac puncture using a heparin (Sigma Aldrich) coated syringe and EDTA tubes (BD) 2 h following striatal injections. Blood was immediately centrifuged at 2,700×g for 15 min (20° C.) to obtain plasma. Plasma was further centrifuged at 10,000 g for 15 min (4° C.) to generate platelet free plasma. This procedure removes large particles such as apoptotic bodies.

Quantitation of Plasma EVs: Dynabeads M-450 Epoxy (Invitrogen) were coupled with anti-GFP antibody (Thermo Fisher) at a ratio of 200 µg antibody per $4\times10^8$ beads. Plasma from GFAP-GFP mouse (50 µL) was incubated with $2\times10^7$ anti-GFP antibody-coupled Dynabeads at 4° C. overnight. The beads were washed and placed on a magnet to separate EVs bound to anti-GFP antibody-coupled Dynabeads. The precipitated EVs were eluted using 0.1 M glycine (pH 3.0). The concentration of immunoprecipitated GFP+EVs was quantified using ZetaView nanoparticle tracking analysis (Particle Metrix) as described above.

Western analysis: Proteins were resolved by 10% SDS-polyacrylamide gel electrophoresis and transferred to polyvinylidene difluoride membranes (Bio-Rad). Nonspecific binding sites were blocked with 5% (w/v) milk in TBS containing 0.1% Tween 20 (TBS-T). After blocking, blots were incubated overnight with the primary polyclonal antibodies to GFP (1:1000; Thermo Fisher) CD63 (1:200; Santa Cruz Biotechnology), flotillin1 (1:1000; Abcam), TSG101 (1:1000; BD Biosciences), mitofilin (1:5000 Thermo Fisher Scientific) and α-actinin (1:1000; Gentex). After washes with TBS-T, blots were incubated for 2 h with the corresponding IgG horseradish peroxidase-linked secondary antibody (1:1000; Cell Signaling Technology) and developed by enhanced chemiluminescence. Image analysis was performed using a G: BOX imaging system (Syngene).

Cytokine measurements: RNA was isolated from fresh frozen tissues (10 to 50 mg) using the RNeasy Mini Kit (Qiagen). Total RNA was reverse-transcribed and quantified using previously published methods. (Westberry, et al., 2010) For quantitative real-time PCR (qRT-PCR), each reaction contained SYBR Green Master Mix (12.5 mL; Life Technologies), diethyl pyrocarbonate $H_2O$ (10.5 mL), forward and reverse primers to CCL2, TNFα, IL-6, IL-1b, IL-17a, IL-10, IGFR1, and CXCL1 (0.5 mL each; Sigma-Aldrich), and cDNA (1 mL). Each 96-well plate included a nontemplate control, and samples were analyzed in triplicate on an Applied Biosystems 7300 (Life Technologies). Cycling parameters were as follows: one cycle for 2 min at 50° C., one cycle for 10 min at 95° C., and 40 cycles for 15 s at 95° C. and for 1 min at 60° C. The change in threshold cycle (ΔCt) for each sample was normalized to β-actin, and ΔΔCt was calculated by comparing ΔCt for the treatment group to the average ΔCt of the control group. Livak and Schmittgen, 2001.

Immunohistochemistry: Coronal brain sections (30 µm) were prepared using a cryostat microtome (Leica). Endogenous peroxidase activity was quenched using a 1% solution of H2O2 in methanol, and primary antibody Ly6b (1:1000, AbD Serotec), was incubated at 4° C. overnight. Sections were washed (3×PBS), and biotinylated secondary antibody (1:100, Vector Laboratories) was added at room temperature for 2 hours. Staining was visualized using an avidin-biotin complex (1:100 of A and B, Vector Laboratories) and DAB-HCl using a microscope to monitor staining progression. Stereological quantitation was performed using a one-in-five series (270-µm spacing), from the rostral point of bregma+1.10 mm to the caudal point of bregma −0.58 mm as previously described. (Chen, et al., 2013)

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Alessenko, A. V., Bugrova, A. E., and Dudnik, L. B. (2004) Connection of lipid peroxide oxidation with the sphingomyelin pathway in the development of Alzheimer's disease, Biochem Soc Trans 32, 144-146.

Asai, H., Ikezu, S., Tsunoda, S., Medalla, M., Luebke, J., Haydar, T., Wolozin, B., Butovsky, O., Kugler, S., and Ikezu, T. (2015) Depletion of microglia and inhibition of exosome synthesis halt tau propagation, Nat Neurosci 18, 1584-1593.

Cutler, R. G., Pedersen, W. A., Camandola, S., Rothstein, J. D., and Mattson, M. P. (2002) Evidence that accumulation of ceramides and cholesterol esters mediates oxidative stress-induced death of motor neurons in amyotrophic lateral sclerosis, Ann Neurol 52, 448-457.

Dickens, A. M., Tovar-y-Romo, L. B., Yoo, S. W., Trout, A. L., Bae, M., Kanmogne, M., Megra, B., Williams, D. W., Witwer, K., Gacias, M., Tabatadze, N., Cole, R., Casaccia, P., Berman, J. W., Anthony, D. C., and Haughey, N. J. (2017) Astrocyte-Shed Extracellular Vesicles Regulate the Leukocyte Response to Inflammatory Brain Lesions. Science Signaling, 10 (473), eaai7696.

Dinkins, M. B., Dasgupta, S., Wang, G., Zhu, G., and Bieberich, E. (2014) Exosome reduction in vivo is associated with lower amyloid plaque load in the 5XFAD mouse model of Alzheimer's disease, Neurobiol Aging 35, 1792-1800.

Dinkins, M. B., Enasko, J., Hernandez, C., Wang, G., Kong, J., Helwa, I., Liu, Y., Terry, A. V., Jr., and Bieberich, E. (2016) Neutral Sphingomyelinase-2 Deficiency Ameliorates Alzheimer's Disease Pathology and Improves Cognition in the 5XFAD Mouse, J Neurosci 36, 8653-8667.

Airola, M. V., Shanbhogue, P., Shamseddine, A. A., Guja, K. E., Senkal, C. E., Maini, R., Bartke, N., Wu, B. X., Obeid, L. M., Garcia-Diaz, M., and Hannun, Y. A., Expression of human nSMase2 and activity assay to identify nSMAse2 inhibitors, PlosOne May 26, 2015, doi:10.137/joumalpone.0124481.

Figuera-Losada, M., Stathis, M., Dorskind, J. M., Thomas, A. G., Bandaru, V. V., Yoo, S. W., Westwood, N. J., Rogers, G. W., McArthur, J. C., Haughey, N. J., Slusher, B. S., and Rojas, C. (2015) Cambinol, a novel inhibitor of neutral sphingomyelinase 2 shows neuroprotective properties, PLoS One 10, e0124481.

Filippov, V., Song, M. A., Zhang, K., Vinters, H. V., Tung, S., Kirsch, W. M., Yang, J., and Duerksen-Hughes, P. J. (2012) Increased ceramide in brains with Alzheimer's and other neurodegenerative diseases, J Alzheimers Dis 29, 537-547.

Haughey, N. J., Cutler, R. G., Tamara, A., McArthur, J. C., Vargas, D. L., Pardo, C. A., Turchan, J., Nath, A., and Mattson, M. P. (2004) Perturbation of sphingolipid metabolism and ceramide production in HIV-dementia, Ann Neurol 55, 257-267.

Horres, C. R., and Hannun, Y. A. (2012) The roles of neutral sphingomyelinases in neurological pathologies, Neurochem Res 37, 1137-1149.

Inglese, J., Auld, D. S., Jadhav, A., Johnson, R. L., Simeonov, A., Yasgar, A., Zheng, W., and Austin, C. P. (2006) Quantitative high-throughput screening: a titration-based approach that efficiently identifies biological activities in large chemical libraries, Proc Natl Acad Sci USA 103, 11473-11478.

Jana, A., and Pahan, K. (2004) Human immunodeficiency virus type 1 gp120 induces apoptosis in human primary neurons through redox-regulated activation of neutral sphingomyelinase, J Neurosci 24, 9531-9540.

Jana, A., and Pahan, K. (2010) Sphingolipids in multiple sclerosis, Neuromolecular Med 12, 351-361.

Li, J., Yu, W., Tiwary, R., Park, S. K., Xiong, A., Sanders, B. G., and Kline, K. (2010) alpha-TEA-induced death receptor dependent apoptosis involves activation of acid sphingomyelinase and elevated ceramide-enriched cell surface membranes, Cancer Cell Int 10, 40.

Luberto, C., Hassler, D. F., Signorelli, P., Okamoto, Y., Sawai, H., Boros, E., Hazen-Martin, D. J., Obeid, L. M., Hannun, Y. A., and Smith, G. K. (2002) Inhibition of tumor necrosis factor-induced cell death in MCF7 by a novel inhibitor of neutral sphingomyelinase, J Biol Chem 277, 41128-41139.

Marks, N., Berg, M. J., and Saito, M. (2008) Glucosylceramide synthase decrease in frontal cortex of Alzheimer brain correlates with abnormal increase in endogenous ceramides: consequences to morphology and viability on enzyme suppression in cultured primary neurons, Brain Res 1191, 136-147.

McCluskey, L., Campbell, S., Anthony, D., and Allan, S. M. (2008) Inflammatory responses in the rat brain in response to different methods of intracerebral administration, J Neuroimmunol 194, 27-33.

Mielke, M. M., Bandaru, V. V., McArthur, J. C., Chu, M., and Haughey, N. J. (2010) Disturbance in cerebral spinal fluid sphingolipid content is associated with memory impairment in subjects infected with the human immunodeficiency virus, J Neurovirol 16, 445-456.

Mielke, M. M., Haughey, N. J., Bandaru, V. V., Schech, S., Carrick, R., Carlson, M. C., Mon, S., Miller, M. I., Ceritoglu, C., Brown, T., Albert, M., and Lyketsos, C. G. (2010) Plasma ceramides are altered in mild cognitive impairment and predict cognitive decline and hippocampal volume loss, Alzheimers Dement 6, 378-385.

Rais, R., Jancarik, A., Tenora, L., Nedelcovych, M., Alt, J., Englert, J., Rojas, C., Le, A., Elgogary, A., Tan, J., Monincova, L., Pate, K., Adams, R., Ferraris, D., Powell, J., Majer, P., and Slusher, B. S. (2016) Discovery of 6-Diazo-5-oxo-1-norleucine (DON) Prodrugs with Enhanced CSF Delivery in Monkeys: A Potential Treatment for Glioblastoma, J Med Chem 59, 8621-8633.

Satoi, H., Tomimoto, H., Ohtani, R., Kitano, T., Kondo, T., Watanabe, M., Oka, N., Akiguchi, I., Furuya, S., Hirabayashi, Y., and Okazaki, T. (2005) Astroglial expression of ceramide in Alzheimer's disease brains: a role during neuronal apoptosis, Neuroscience 130, 657-666.

Trajkovic, K., Hsu, C., Chiantia, S., Rajendran, L., Wenzel, D., Wieland, F., Schwille, P., Brugger, B., and Simons, M. (2008) Ceramide triggers budding of exosome vesicles into multivesicular endosomes, Science 319, 1244-1247.

Wang, G., Silva, J., Dasgupta, S., and Bieberich, E. (2008) Long-chain ceramide is elevated in presenilin 1 (PS1M146V) mouse brain and induces apoptosis in PS1 astrocytes, Glia 56, 449-456.

Wheeler, D., Knapp, E., Bandaru, V. V., Wang, Y., Knorr, D., Poirier, C., Mattson, M. P., Geiger, J. D., and Haughey, N. J. (2009) Tumor necrosis factor-alpha-induced neutral sphingomyelinase-2 modulates synaptic plasticity by controlling the membrane insertion of NMDA receptors, J Neurochem 109, 1237-1249.

Wu, B. X., Clarke, C. J., and Hannun, Y. A. (2010) Mammalian neutral sphingomyelinases: regulation and roles in cell signaling responses, Neuromolecular Med 12, 320-330.

Lee, Y., El Andaloussi, S. and Wood, M. J. (2012) Exosomes and microvesicles: extracellular vesicles for genetic information transfer and gene therapy. Hum Mol Genet 21, R125-134.

Lotvall, J. et al. (2014) Minimal experimental requirements for definition of extracellular vesicles and their functions: a position statement from the International Society for Extracellular Vesicles. J Extracell Vesicles 3, 26913.

von der Malsburg, K. et al. (2011) Dual role of mitofilin in mitochondrial membrane organization and protein biogenesis. Dev Cell 21, 694-707.

Sjoblom, B., Salmazo, A. and Djinovic-Carugo, K. (2008) Alpha-actinin structure and regulation. Cell Mol Life Sci 65, 2688-2701.

Shin, J. T. et al. (1996) Serum-starvation induces the extracellular appearance of FGF-1. Biochim Biophys Acta 1312, 27-38.

Gu, L. et al. (2013) Early activation of nSMase2/ceramide pathway in astrocytes is involved in ischemia-associated neuronal damage via inflammation in rat hippocampi. J Neuroinflammation 10, 109.

Back, M. J. et al. (2018) Activation of neutral sphingomyelinase 2 by starvation induces cell-protective autophagy via an increase in Golgilocalized ceramide. Cell Death & Disease 9, 670.

Mathias, S. et al. (1993) Activation of the sphingomyelin signaling pathway in intact EL4 cells and in a cell-free system by IL-1 beta. Science 259, 519-522.

Westberry, J. M., Trout, A. L. and Wilson, M. E. (2010) Epigenetic regulation of estrogen receptor alpha gene expression in the mouse cortex during early postnatal development. Endocrinology 151, 731-740.

Livak, K. J. and Schmittgen, T. D. (2001) Analysis of relative gene expression data using real-time quantitative PCR and the 2(−Delta C(T)) Method. Methods 25, 402-408.

Chen, X., Hui, L., Geiger, N. H., Haughey, N. J. and Geiger, J. D. (2013) Endolysosome involvement in HIV-1 transactivator protein-induced neuronal amyloid beta production. Neurobiol Aging 34, 2370-2378.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating one or more diseases associated with neutral sphingomyelinase 2 (nSMase2) in a subject in need of treatment thereof, the method comprising administering to the subject a therapeutically effective amount of 2,6-dimethoxy-4-(5-phenyl-4-thiophen-2-yl-1H-imidazol-2-yl)-phenol (DPTIP) or a pharmaceutically acceptable salt thereof wherein the one or more diseases associated with nSMase2 is selected from a neurodegenerative disease or an oncologic disease.

2. The method of claim 1, wherein the neurodegenerative disease is selected from the group consisting of Alzheimer's disease (AD), multiple sclerosis (MS), amyotrophic lateral sclerosis (ALS), and HIV-associated neurocognitive disorders (HAND).

* * * * *